USO05525735A

United States Patent [19]
Gallop et al.

[11] Patent Number: 5,525,735
[45] Date of Patent: Jun. 11, 1996

[54] METHODS FOR SYNTHESIZING DIVERSE COLLECTIONS OF PYRROLIDINE COMPOUNDS

[75] Inventors: Mark A. Gallop, Los Altos; Martin A. Murphy, Mountain View, both of Calif.

[73] Assignee: AFFYMAX Technologies NV, Curacao, Netherlands Antilles

[21] Appl. No.: 354,309

[22] Filed: Dec. 12, 1994

Related U.S. Application Data

[63] Continuation-in-part of Ser. No. 264,136, Jun. 22, 1994.
[51] Int. Cl.⁶ .................. C07D 207/00; C07D 209/00
[52] U.S. Cl. .................. 548/533; 548/400; 548/406; 548/453; 548/517; 548/518; 548/532; 548/536; 548/541; 548/560; 548/565; 548/566; 548/570; 548/577; 548/537; 530/323; 435/7.92; 436/518
[58] Field of Search .................. 548/400, 532, 548/533, 536, 537; 530/323

[56] References Cited

U.S. PATENT DOCUMENTS 5,143,854   9/1992   Pirrung et al. .................. 436/518

FOREIGN PATENT DOCUMENTS

| 91/05058 | 4/1991 | WIPO . |
| 91/17271 | 11/1991 | WIPO . |
| 91/19818 | 12/1991 | WIPO . |
| 92/02536 | 2/1992 | WIPO . |
| 93/08278 | 4/1993 | WIPO . |
| 9306121 | 4/1993 | WIPO . |

OTHER PUBLICATIONS

Tsuge et al., 1989, Advances in Heterocyclic Chemistry, 45: pp. 231–349, Recent advances in azomethine ylide chemistry.

Cwirla et al., 1990, P.N.A.S. USA, 87: pp. 6378–6382, Peptides on phage: A vast library of peptides for identifying ligands.

Scott et al., 1990, Science 249: pp. 386–390, Searching for Peptide Ligands with an Epitope Library.

Devlin et al., 1990, Science, 249: pp. 404–406, Random Peptide Libraries: A Source of Specific Protein Binding Molecules.

Ardill et al., 1988, Tetrahedron, 44: pp. 4953–4966, X=Y–ZH systems as potential 1,3–Dipoles. Part 19. Intramolecular cycloadditions of non–stabilised azomethine ylides generated via the decarboxylative route from amino acids.

Dorrity et al., 1988, Tetrahedron, 44: pp. 4941–4952, X=Y–ZH systems as potential 1,3–Dipoles. Part 18. Cycloaddition of 4π–sulphinylaminomethamide species generated from α–amino acids and α–amino acid esters by sulphonyl group transfer. X–ray crystal structure of 4–Iso–propyl–7–methyl–3,7–diazobicyclo(3.3.0) octane S–oxide.

Grigg et al., 1989, Tetrahedron, 45: pp. 1723–1746, X=Y–ZH systems as potential 1,3–dipoles. Part 21. Activation of the ZH in imines.

Grigg, 1987, Chem. Soc. Rev., 16: pp. 89–121, Prototropic routes to 1,3– and 1,5–dipoles, and 1,2–ylides: Applications to the synthesis of heterocyclic compounds.

Barr et al., 1989, Tetrahedron Ltrs. 30: pp. 4727–4730, Ti(V) mediated transesterification and regio–and–stereo–specific cycloaddition of imines of α–amino esters. Reversal of normal regiochemistry.

Allway et al., 1991, Tetrahedron Ltrs., 32: pp. 5817–5820, Chiral Co(II) and Mn(II) catalysts for the 1,3–dipolar cycloaddition reactions of azomethine ylides derived from arylidene imines of glycine.

Barr et al., 1990, Tetrahedron Ltrs., 31: pp. 6569–6572, Metal ion catalysed asymmetric 1,3–dipolar cycloaddition reactions of imnes of α–amino esters.

Grigg et al., 1980, Tetrahedron Ltrs. 21: pp. 2461–2464, X=Y–ZH systems as potential 1,3–dipoles. The stereochemistry and regiochemistry of cycloaddition reactions of imines of α–amino–acid esters.

Barr et al., 1988, Tetrahedron, 44: pp. 557–570, X=Y–ZH systems as potential 1,3–dipoles. Part 15. Amine generated azaallyl anions versus metallo–1,3–dipoles in cycloadditions of α–amino acid esters. Facile regio– and stereo–specific formation of pyrrolidines.

Amornraska et al., 1989, Tetrahedron, 45: 4649–4668, X=H–ZH compounds as potential 1,3–dipoles. Part 24. Preparation and thermal fragmentation of imidazolidines. Influence of metal salts on pyrolidine versus imidazolidine formation.

Armstrong et al., 1985, Tetrahedron, 41: pp. 3547–3558, X=Y–ZH systems as potential 1,3–dipoles–5.

Grigg et al., 1993, Tetrahedron., 49: pp. 8679–8690, Chiral azomethine ylides from homochiral cyclic α–amino esters. Unusual regiospecific deprotonation of iminium ions.

Grigg et al., 1992, Tetrahedron, 48: pp. 10431–10442, Metallo–azomethine ylides from alphatic aldimines. Facile regio– and stereo–specific cycloddition reactions.

Grigg et al., 1987, Tetrahedron., 43: pp. 5887–5898, X=Y–ZH systems as potential 1,3–dipoles. Part 14. Bronsted and Lewis acid catalysis of cycloadditions of arylidene imines of amino acid esters.

Grigg et al., 1987, J. Chem. Soc. Commun.: pp. 47–51, The decarboxylative route to azomethine ylides. Stereochemistry of 1,3–dipole formation.

Petrillo et al., 1982, Medicinal Research Reviews, 2: pp. 1–41 Angiotensin–converting enzyme inhibitors: medicinal chemistry and biological actions.

Grigg et al., 1983, Tetrahedron Ltrs., 24: pp. 4457–4460, The mechanism of the racemisation of α–amino acids in the presence of aldehydes.

(List continued on next page.)

*Primary Examiner*—Joseph Paul Brust
*Attorney, Agent, or Firm*—Lauren L. Stevens

[57] ABSTRACT

Disclosed are methods for synthesizing very large collections of diverse pyrrolidine compounds and derivatives thereof on solid supports and synthetic compound libraries comprising pyrrolidine groups and derivatives thereof prepared by such methods.

9 Claims, 7 Drawing Sheets

OTHER PUBLICATIONS

Aly et al., 1994, Tetrahedron., 50: pp. 895–906, X=Y–ZH compounds as potential 1,3–dipoles. Part 41. Azomethine ylide formation from the reactions of α–amino acids and esters with alloxan (strecker degradation) and with1–phenyl–3–methylpyrazolin–4,5–dione.

Tsuge et al., 1988, J. Org. Chem., 53: pp. 1384–1391, Lithium bromide/triethylamine induced cycloaddition of N–alkylidene 2–amino esters and amides to electron–deficient olefins with high regio–and stereoselectivity.

Cheung et al., 1973, Biochimica et Biophysica Acta, 293: pp. 451–463, Inhibition of homogeneous angiotensin–converting enzyme of rabbit lung by synthetic venom peptides of bothrops jararaca.

Ellman, 1959, Archives of Biochemistry and Biophysics, 82: pp. 70–77 Tissue sulfhydryl groups.

Furka et al., 1991, Int. J. Peptide Protein Res., 37: pp. 487–493 General method for rapid synthesis of multicomponent peptide mixtures.

Bull et al., 1985, J. of Biological Chem., 260: pp. 2952–2962, Inhibition of rabbit lung angiotensin–converting enzyme by N alpha–[(S)–1–carboxy–3–phenylpropyl] L–alanyl–L–proline and N alpha–[(S)–carboxy–3–phenylpropyl] L–lysyl–L–proline.

Gallop et al., 1994, J. of Medicinal Chem., 37: pp. 1233–1251, Perspectives of combinatorial technologies to drug discovery. 1. Background and peptide combinatorial libraries.

Gordon et al., 1994, J. of Medicinal. Chem., 37: pp. 1385–1401, Applications of combinatorial technologies to drug discovery. 2. Combinatorial organic synthesis, library screening strategies, and future directions.

Williams et al., 1992, J. Org. Chem., 57: pp. 6527–6532, Asymetric [1,3]–dipolar cycloaddition reactions: Synthesis of highly substituted proline derivatives.

Cull et al., 1992, P.N.A.S. USA, 89: pp. 1865–1869, Screening for receptor ligands using large libraries of peptides linked to the C terminus of the lac repressor.

METHODS FOR SYNTHESIZING DIVERSE COLLECTIONS OF PYRROLIDINE COMPOUNDS

CROSS REFERENCE TO RELATED APPLICATIONS

This application is a continuation-in-part of Ser. No. 08/264,136, filed Jun. 22, 1994, which is expressly incorporated herein by reference for all purposes.

BACKGROUND OF THE INVENTION

1. Field of the Invention

This invention is directed to methods for synthesizing very large collections of diverse pyrrolidine compounds on solid supports. This invention is further directed to methods for identifying and isolating pyrrolidine compounds with useful and diverse activities from such collections. This invention is still further directed to the incorporation of identification tags in such collections to facilitate identification of compounds with desired properties.

2. References

The following publications, patents and patent applications are cited in this application as superscript numbers:

[1] Tsuge, et al., *Recent Advances in Azomethine Ylide Chemistry*, in "Advances in Heterocyclic Chemistry", Vol. 45, pp. 231–349, Academic Press, Inc. (1989)
[2] Cwirla, et al., *Proc. Natl. Acad. Sci., USA*, 87:6378–6382 (1990)
[3] Scott & Smith, *Science*, 249:386–390 (1990)
[4] Devlin, et al., *Science*, 249:404–406 (1990)
[5] Cull, et al., *Proc. Natl. Acad. Sci., USA*, 89:1865–1869 (1992)
[6] International Patent Application Publication No. WO 91/17271
[7] International Patent Application Publication No. WO 91/19818
[8] International Patent Application Publication No. WO 93/08278
[9] International Patent Application Publication No. WO 91/05058
[10] International Patent Application Publication No. WO 92/02536
[11] International Patent Application Publication No. WO 93/06121
[12] U.S. patent application Ser. No. 07/946,239
[13] U.S. Pat. No. 5,143,854, issued Sep. 1, 1992
[14] Adrill, et al., *Tetrahedron*, 44(15):4953–4966 (1988)
[15] Dorrity, et al., *Tetrahedron*, 44(15):4941–4952 (1988)
[16] Grigg, et al., *Tetrahedron*, 45(6):1723–1746 (1989)
[17] Grigg, *Chem. Soc. Rev.*, 16:89–121 (1987)
[18] Barr, et al, *Tetrahedron Letters*, 30(35):4727–4730 (1989)
[19] Allway, et al., *Tetrahedron Letters*, 32(41):5817–5820 (1991)
[20] Barr, et al., *Tetrahedron Letters*, 31(45):6569–6572 (1990)
[21] Grigg, et al., *Tetrahedron Letters*, 21:2461–2464 (1980)
[22] Barr, et al., *Tetrahedron*, 44(2):557–570 (1988)
[23] Amornraksa, et al., *Tetrahedron*, 45:(14):4649–4668 (1989)
[24] Armstrong, et al., *Tetrahedron*, 41:(17):3547–3558 (1985)
[25] Grigg, et al., *Tetrahedron*, 49(38):8679–8690 (1993)
[26] Grigg, et al., *Tetrahedron*, 48(47):10431–10442 (1992)
[27] Grigg, et al., *Tetrahedron*, 43(24):5887–5898 (1987)
[28] Grigg, et al., *J. Chem. Soc. Chem. Commun.*, pp. 47–51 (1987)
[29] Grigg, et al., *Tetrahedron*, 48(47):10423–10430 (1992)
[30] Grigg, et al., *Tetrahedron Letters*, 24(41):4457–4460 (1983)
[31] Aly, et al., *Tetrahedron*, 50(3):895–906 (1994)
[32] Tsuge, et al., *J. Org. Chem.* 53:1384–1391 (1988)
[33] Cheung and Cushman, *Biochim. Biophys. Acta* 293:451–463 (1973)
[34] Ellman, *Arch. Biochem. Biophys.* 82:70 (1959)
[35] Furka, et al., *Int. J. Pept. Protein Res.* 37:487–493 (1991)
[36] Petrillo and Ondetti, *Med. Res. Rev.*, 2:1–41 (1982)
[37] Bull, et al., *J. Biol. Chem.*, 260:2952–2962 (1985)
[38] Gallop, et al., *J. Med. Chem.*, 37:1233–1241 (1994) and
[39] Gordon, et al., *J. Med. Chem.*, 37:1385–1401 (1994)

All of the above publications, patents and patent applications are herein incorporated by reference in their entirety to the same extent as if each individual publication, patent or patent application was specifically and individually indicated to be incorporated by reference in its entirety.

STATE OF THE ART

Ligands for macromolecular receptors can be identified by screening diverse collections of compounds, e.g., peptides, produced through either molecular biological or synthetic chemical techniques. For example, recombinant peptide libraries have been generated by inserting degenerate oligonucleotides into genes encoding capsid proteins of filamentous bacteriophage and the DNA-binding protein Lac I.[2-8] These random libraries contain more than $10^9$ different peptides, each fused to a larger protein sequence that is physically linked to the genetic material encoding it. Such libraries are efficiently screened for interaction with a receptor by several rounds of affinity purification, the selected exposition or display vectors being amplified in *E. coli* and the DNA of individual clones sequenced to reveal the identity of the peptide responsible for receptor binding.[9,10]

Other disclosed methods for screening libraries of compounds for binding properties to a receptor include methods wherein each member of the library is tagged with a unique identifier tag to facilitate identification of compounds having binding properties[11,12] or where the library comprises a plurality of compounds synthesized at specific locations on the surface of a solid substrate wherein the receptor is appropriately labeled to identify binding, e.g., fluorescent or radioactive labels. Correlation of the labelled receptor bound to the substrate with its location on the substrate identifies the binding ligand.[13]

Central to these methods is the screening of a multiplicity of compounds in the library and the ability to identify the structures of the compounds which have a requisite binding affinity for the receptor. Preferably, in order to facilitate synthesis and identification, the compounds in the library are typically formed on solid supports wherein the compound is covalently attached to the support via a cleavable or noncleavable linking arm. In this regard, the diversity of naturally occurring amino acids permits the generation of extensive peptide libraries on such solid supports without resort to the use of synthetic amino acids which can include derivatives of naturally occurring amino acids. These libraries are then screened to identify "lead compounds" having good binding affinity to the receptor.

Pharmaceutical drug discovery relies heavily on studies of structure-activity relationships wherein the structure of "lead compounds" is typically altered to determine the effect of the alteration on activity. When the lead compound comprises one or more amino acids (e.g., a peptide), alteration of the structure of one or more of the amino acid(s) permits evaluation of the effect of the structural alteration on activity. Thus libraries of compounds derived from a lead compound can be created by including derivatives of the amino acids in the peptides and repeating the screening procedures.[38,39]

The use of such amino acid derivatives in these libraries has been disclosed in the art.[12,13] Ideally, the amino acid derivative is synthesized in situ on the solid support so that the support can be tagged to identify the synthetic steps employed and/or the derivative incorporated onto the support. However, relatively simple synthetic methods to produce a diverse collection of such derivatives on the supports are often not available.

One particular class of compounds which would be useful for inclusion in screening libraries are pyrrolidine compounds, including proline and derivatives thereof. These compounds form the basis of an important class of compounds having diverse pharmaceutical and chemical properties. Pyrrolidine compounds are the central skeletal feature on numerous alkaloids.[1] In addition, proline, itself, is often included in the structure of peptides having receptor binding activity and derivatives of proline form important pharmaceutical compositions such as Captopril, a commercial antihypertensive agent and inhibitor of angiotensin-converting enzyme (ACE).

The inclusion of certain proline derivatives into such libraries is well known in the art. However, a simple procedure for the in situ incorporation of a multiplicity of pyrrolidine derivatives on solid supports is not previously known. The ability to synthesize a multiplicity of pyrrolidine derivatives on a solid support or on different solid supports would enhance the structural variation of a library and provide important structure-activity information.

SUMMARY OF THE INVENTION

This invention is directed to general synthetic methods for incorporating a pyrrolidinyl group on a solid support which methods can be employed in conjunction with known stochastic methods for preparing libraries of compounds comprising one or more pyrrolidinyl groups.

Solid supports containing such pyrrolidinyl groups preferably comprise a linking arm which links the solid support to the compound. The linking arm can be either cleavable or non-cleavable and when cleavable, can be used to prepare a library of soluble compounds. The library of compounds on the solid support comprises monomers and sequences of monomers (e.g., oligomers and polymers), the monomers employed with such oligomers and polymers being any member of the set of molecules which can be joined together to form an oligomer or polymer (e.g., amino acids, carbamates, sulfones, sulfoxides, nucleosides, carbohydrates, ureas, phosphonates, lipids, esters, combinations of the same, and the like). In the case of a library of monomers, the compound attached to the solid support is a pyrrolidine compound and, in the case of libraries of oligomers and polymers, at least one of the monomers of the oligomer and polymer is a pyrrolidinyl group.

The library is screened to isolate individual compounds that bind to a receptor or possess some desired property. In a preferred embodiment, each compound in the library is unique.

Accordingly, in one of its method aspects, this invention is directed to a method for synthesizing a pyrrolidinyl group covalently attached to a solid support which method comprises:

(a) selecting a solid support comprising at least one compound covalently attached thereto which compound comprises a moiety selected from the group consisting of a complementary group having at least one site of carbon-carbon unsaturation and an azomethine ylide precursor;

(b) converting said moiety to a pyrrolidinyl group.

The solid supports prepared in the methods described above can be used, for example, in creating libraries of compounds in the manner described in International Patent Application Publication No. WO 93/06121 or in the solid supports described in U.S. Pat. No. 5,143,854, to screen said compounds for binding affinity to ligands.

Accordingly, in another of its method aspects, this invention is directed to a method for preparing a synthetic compound library produced by synthesizing on each of a plurality of solid supports a single compound wherein each compound comprises at least one pyrrolidinyl group, which library is synthesized in a process comprising:

a) apportioning the supports comprising a covalently bound azomethine ylide precursor or a covalently bound complementary group comprising at least one site of carbon-carbon unsaturation among a plurality of reaction vessels;

b) exposing the supports in each reaction vessel under conditions wherein the azomethine ylide precursor or the complementary group is converted to a pyrrolidinyl group wherein said pyrrolidinyl group is different for each of the reaction vessels; and c) optionally, pooling the supports.

In one embodiment procedures a) through c) are conducted only once whereas in another embodiment procedures a) through c) are repeated up to about 20 times.

If procedure a) through c) are conducted only once, then the resulting library comprises a library of different pyrrolidine compounds covalently attached to the solid support. These pyrrolidine compounds can be either directly attached or linked to the solid support or can be part of a larger molecule already synthesized on the support. According to another embodiment, these pyrrolidine compounds are cleaved from the solid support.

If procedures a) through c) are conducted a multiple number of times, then each of the resulting compounds is an oligomer/polymer.

Preferably, in the methods described above, the azomethine ylide precursor is converted to the pyrrolidinyl group by converting this precursor to an azomethine ylide which is then reacted with a complementary compound having at least one site of carbon-carbon unsaturation so as to form a pyrrolidinyl group. Likewise, the complementary group or moiety having at least one site of carbon-carbon unsaturation is preferably converted to a pyrrolidinyl group by reaction with an azomethine ylide.

In still another of its method aspects, this invention is directed to a method for preparing a synthetic compound library produced by synthesizing on each of a plurality of solid supports a single compound, wherein each compound comprises a pyrrolidinyl group, which library is synthesized in a process comprising:

a) apportioning the supports among a plurality of reaction vessels;

b) exposing the supports in each reaction vessel to a first monomer under conditions wherein the first monomer becomes covalently linked to the support wherein said first monomer is different for each of the reaction vessels;

c) pooling the supports; and d) optionally repeating procedures a) through c) up to about 20 times;

wherein at least one of the monomers employed in procedure b) comprises a moiety selected from the group consisting of a complementary compound having at least one site of carbon-carbon unsaturation and a group convertible to an azomethine ylide precursor which moiety is converted to a pyrrolidinyl group prior to procedure c).

In the case, where the monomer contains a moiety convertible to an azomethine ylide precursor, conversion to the pyrrolidinyl group is achieved by first converting this moiety to an azomethine ylide precursor, then to the azomethine ylide followed by reaction with a complementary compound having at least one site of carbon-carbon unsaturation. As before, conversion of a complementary compound having at least one site of carbon-carbon unsaturation to the pyrrolidinyl group is by reaction with an azomethine ylide.

Moieties convertible to azomethine ylide precursors include aldehyde and ketone moieties as well as primary amines having a methine hydrogen atom alpha to the amino group. Such moieties are readily convertible to imines having a methine or methylene hydrogen atom alpha to the amino group which, as noted below, are azomethine ylide precursors.

In a preferred embodiment for each of the above described methods, the azomethine ylide precursor is an imine group having a methine or methylene hydrogen atom alpha to the nitrogen atom of the imine group or is convertible to such an imine group which is preferably linked to the solid support through a linking arm.

In a further preferred embodiment for each of the above described methods, the resulting pyrrolidinyl group comprises a secondary amino group in the ring structure which can optionally be employed to further modify the pyrrolidinyl group.

In one of its composition aspects, this invention is directed to a synthetic compound library comprising a plurality of different compounds each compound covalently linked to a solid support wherein each of said compounds comprise at least one pyrrolidinyl group which group is prepared by the method which comprises (a) selecting a solid support comprising at least one compound attached thereto which compound comprises a moiety selected from the group consisting of a complementary group having at least one site of carbon-carbon unsaturation and an azomethine ylide precursor;

(b) converting said moiety to a pyrrolidinyl group.

In one embodiment, each compound of said plurality of different compounds is covalently linked to the same solid support in the manner described in U.S. Pat. No. 5,143,854. In another embodiment, each compound of said plurality of different compounds is covalently linked to a different solid support in the manner described in International Patent Application Publication No. WO 93/06121. Both U.S. Pat. No. 5,143,854 and International Patent Application Publication No. 93/06121 are incorporated herein by reference in their entirety. In yet another embodiment, each compound, or a portion thereof, is cleaved from the solid support to yield a soluble synthetic compound library.

In one preferred embodiment, the —NH moiety of the pyrrolidinyl group is used to incorporate this group into a peptide compound wherein the pyrrolidinyl group is located at any point in the peptide sequence. In another preferred embodiment, the —NH moiety of the pyrrolidinyl group is modified by acylation, sulfonylation, alkylation and the like to form a variety of pyrrolidinyl derivatives.

In yet another preferred embodiment, the library comprises a plurality of pyrrolidinyl monomers (compounds) which are screened for biological or pharmaceutical activity.

DETAILED DESCRIPTION OF THE INVENTION

This invention is directed to synthetic methods for preparing pyrrolidinyl groups in situ on solid supports and the use of these methods to incorporate pyrrolidinyl groups in large synthetic compound libraries.

Prior to discussing this invention in further detail, the following terms will first be defined:

The term "substrate" or "solid support" refers to a material having a rigid or semi-rigid surface which contain or can be derivatized to contain reactive functionality which covalently links a compound to the surface thereof. Such materials are well known in the art and include, by way of example, silicon dioxide supports containing reactive Si—OH groups, polyacrylamide supports, polystyrene supports, polyethyleneglycol supports, and the like. Such supports will preferably take the form of small beads, pellets, disks, or other conventional forms, although other forms may be used. In some embodiments, at least one surface of the substrate will be substantially flat. Preferred substrates include polystyrene resins preloaded with protected amino acids. More preferably, the amino acids will be protected with the Fmoc group. Particularly preferred substrates include TentaGel™ pre-loaded with Fmoc-protected amino acids at a loading of about 0.5 grams/loading 0.20–0.26 mmol.

The term "azomethine ylide precursor" refers to any group, substituent or functionality which is convertible to an azomethine ylide. Such precursors are known in the art[1, 14-31] and include, by way of example only, aziridines, imines having a methine or methylene hydrogen atom a to the nitrogen atom of the imine, and the like.

The compounds comprising an azomethine ylide precursor can be covalently attached directly to the solid support or can be attached via a linking arm. Linking arms or linkers are well known in the art and include, by way of example only, conventional linking arms such as those comprising ester, amide, carbamate, ether, thio ether, urea, amine groups and the like.

The linking arm can be cleavable or non-cleavable. "Cleavable linking arms" refer to linking arms wherein at least one of the covalent bonds of the linking arm which attaches the compound comprising the pyrrolidinyl group to the solid support can be readily broken by specific chemical reactions thereby providing for compounds comprising pyrrolidinyl groups free of the solid support ("soluble compounds"). The chemical reactions employed to break the covalent bond of the linking arm are selected so as to be specific for bond breakage thereby preventing unintended reactions occurring elsewhere on the compound. The cleavable linking arm is selected relative to the synthesis of the compounds to be formed on the solid support so as to prevent premature cleavage of this compound from the solid support as well as not to interfere with any of the procedures employed during compound synthesis on the support.

Figure 2A:
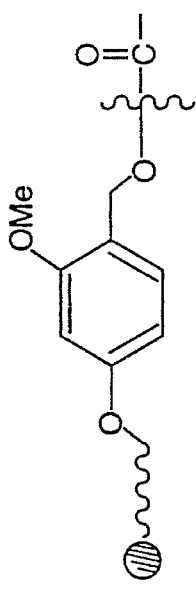
FIG. 2A–2D illustrates several cleavable linking arms for covalently linking compounds comprising at least one pyrrolidinyl group to the solid support.

Suitable cleavable linking arms are well known in the art and FIGS. 2A–2D illustrates several embodiments of such linking arms. Specifically, FIG. 2A illustrates a cleavable Sasrin resin comprising polystyrene beads and a cleavable linking arm as depicted therein which linking arm is cleaved by strong acidic conditions such as trifluoroacetic acid. Cleavage results in breakage at the vertical line interposed between the oxygen and carbonyl moieties of the ester so as to provide for a compound terminating in a carboxylic acid.

Figure 2B:
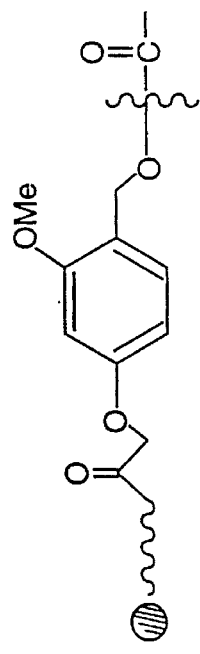
Figure 2C:
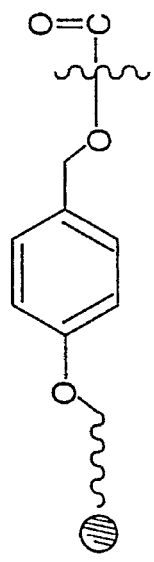

FIGS. 2B and 2C illustrate cleavable TentaGel AC and TentaGel PHB resins respectively, each comprising a polystyrene bead and the cleavable linking arm depicted therein both of which are cleaved by strong acidic conditions such as trifluoroacetic acid. Cleavage results in breakage at the vertical line interposed between the oxygen and carbonyl moieties of the ester so as to provide for a compound terminating in a carboxylic acid.

Figure 2D:
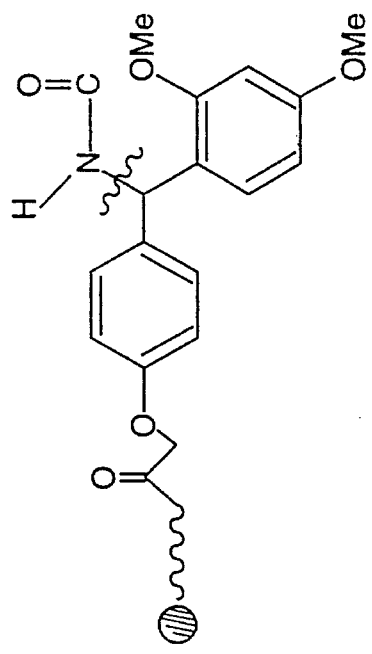

FIG. 2D illustrates a cleavable TentaGel RAM resin comprising a polystyrene bead and a cleavable linking arm depicted therein which is cleaved by strong acidic conditions such as trifluoroacetic acid. Cleavage results in breakage at the vertical line interposed between the nitrogen and the benzhydryl carbon of the linking arm so as to provide for a compound terminating in an amide group. In this case, this linking arm facilitates formation of the amide bond by stabilizing the intermediate carbonium ion on the carbon atom between the two aromatic groups. Such stabilization permits selective bond cleavage as compared to bond cleavage for other amide groups of the compound comprising a pyrrolidinyl group.

Reversible covalent cleavable linkages can be used to attach the molecules to the support. Examples of suitable reversible chemical linkages include (1) a sulfoester linkage provided by, e.g., a thiolated tagged-molecule and a N-hydroxy-succinimidyl support, which linkage can be controlled by adjustment of the ammonium hydroxide concentration; (2) an benzylhydryl or benzylamide linkage provided by, e.g., a Knorr linker, which linkage can be controlled by adjustment of acid concentration; (3) a disulfide linkage provided by, e.g., a thiolated tagged-molecule and a 2-pyridyl disulfide support (e.g., thiolsepharose from Sigma), which linkage can be controlled by adjustment of the DTT (dithiothreitol) concentration; and (4) linkers which can be cleaved with a transition metal (i.e. HYCRAM).

The linker may be attached between the tag and/or the molecule and the support via a non-reversible covalent cleavable linkage. For example, linkers which can be cleaved photolytically can be used. Preferred photoclearable linkers of the invention include 6-nitroveratryoxycarbonyl (NVOC) and other NVOC related linker compounds (see PCT patent publication Nos. WO 90/15070 and WO 92/10092; see also U.S. patent application Ser. No. 07/971, 181, filed 2 Nov. 1992, now abandoned incorporated herein by reference); the ortho-nitrobenzyl-based linker described by Rich (see Rich and Gurwara (1975) *J. Am. Chem. Soc.* 97:1575–1579; and Barany and Albericio (1985) *J. Am. Chem. Soc.* 107: 4936–4942) and the phenacyl based linker discussed by Wang. (see Wang (1976) *J. Org. Chem.* 41:3258; and Bellof and Mutter (1985) *Chimia* 39:10). Other particularly preferred photocleavable linkers are shown below:

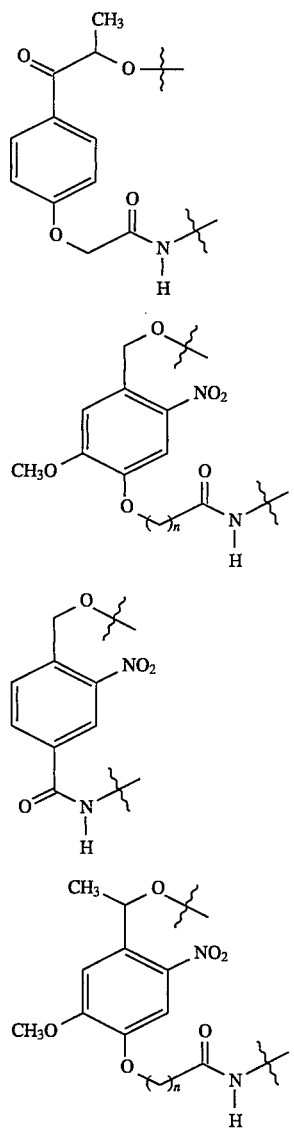

"Non-cleavable linking arms" refer to linking arms wherein one or more of the covalent bonds linking the compound comprising a pyrrolidinyl linking group to the solid support can only be cleaved under conditions which chemically alters unintended parts of the structure of the compound attached thereto.

The term "pyrrolidinyl group" refers to a saturated 5-member ring heterocyclic compound containing one ring nitrogen atom optionally containing vinyl unsaturation between carbons 3 and 4 of the ring. When fully saturated, the pyrrolidinyl group can be depicted as follows:

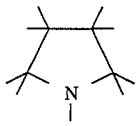

Substituents to the pyrrolidinyl group can occur at any of the ring atoms including the nitrogen atom in the manner depicted above. Such substituents are governed solely by the reagents employed thereby providing flexibility in preparing a large library of pyrrolidinyl compounds. Suitable substituents include, by way of example only:

alkyl groups of from 1 to 10 carbon atoms optionally substituted with 1 or more (typically up to 5) substituents selected from the group consisting of hydroxyl, halo, cyano, amino, mono- and di-alkylamines of from 1 to 10 carbon atoms in the amine group, alkoxy of from 1 to 10 carbon atoms, —SH, —SR where R is alkyl of from 1 to 10 carbon atoms, carboxyl, carboxyl esters of from 1 to 10 carbon atoms in the ester moiety, —NR$^1$C(O)R$^2$ where R$^1$ and R$^2$ are independently selected from the group consisting of hydrogen and alkyl of from 1 to 10 carbon atoms, heterocycles having from 2 to 6 carbon atoms and 1 to 3 ring hetero atoms selected from the group consisting of nitrogen, oxygen and sulfur, aryl groups of from 6 to 10 carbon atoms optionally substituted with from 1 to 3 substituents on the aryl moiety selected from the group consisting of halo, hydroxyl, amino, cyano, carboxyl, nitro, alkyl of from 1 to 10 carbon atoms, alkoxyl of from 12 to 10 carbon atoms, alkoxy of from 1 to 10 carbon atoms optionally substituted with 1 or more (typically up to 5) substituents selected from the group consisting of hydroxyl, halo, cyano, amino, mono- and di-alkylamines of from 1 to 10 carbon atoms in the amine group, alkoxy of from 1 to 10 carbon atoms, —SH, —SR where R is alkyl of from 1 to 10 carbon atoms, carboxyl, carboxyl esters of from 1 to 10 carbon atoms in the ester moiety, —NR$^1$C(O)R$^2$ where R$^1$ and R$^2$ are independently selected from the group consisting of hydrogen and alkyl of from 1 to 10 carbon atoms, heterocycles having from 2 to 6 carbon atoms and 1 to 3 ring hetero atoms selected from the group consisting of nitrogen, oxygen and sulfur, aryl groups of from 6 to 10 carbon atoms optionally substituted with from 1 to 3 substituents on the aryl moiety selected from the group consisting of halo, hydroxyl, amino, cyano, carboxyl, nitro, alkyl of from 1 to 10 carbon atoms, alkoxyl of from 1 to 10 carbon atoms, carboxyl groups, carboxyl ester groups wherein the ester group comprises from 1 to 10 carbon atoms, R—C(O)— groups where R is alkyl of from 1 to 10 carbon atoms optionally substituted on the alkyl group with 1 or more (typically up to 5) substituents selected from the group consisting of hydroxyl, halo, cyano, amino, mono- and di-alkylamines of from 1 to 10 carbon atoms in the amine group, alkoxy of from 1 to 10 carbon atoms, —SH, —SR where R is alkyl of from 1 to 10 carbon atoms, carboxyl, carboxyl esters of from 1 to 10 carbon atoms in the ester moiety, —NR$^1$C(O)R$^2$ where R$^1$ and R$^2$ are independently selected from the group consisting of hydrogen and alkyl of from 1 to 10 carbon atoms, heterocycles having from 2 to 6 carbon atoms and 1 to 3 ring hetero atoms selected from the group consisting of nitrogen, oxygen and sulfur, aryl groups of from 6 to 10 carbon atoms optionally substituted with from 1 to 3 substituents on the aryl moiety selected from the group consisting of halo, hydroxyl, amino, cyano, carboxyl, nitro, alkyl of from 1 to 10 carbon atoms, alkoxyl of from 1 to 10 carbon atoms, aryl groups of from 6 to 10 carbon atoms optionally from 1 to 3 substituents on the aryl moiety selected from the group consisting of halo, hydroxyl, amino, cyano, carboxyl, nitro, alkyl of from 1 to 10 carbon atoms, alkoxyl of from 1 to 10 carbon atoms.

In one embodiment, the pyrrolidinyl group contains a carboxyl substituent alpha to the nitrogen ring atom to provide for proline derivatives. It being understood that such proline derivatives are a preferred subclass of the herein described pyrrolidinyl groups.

In another embodiment, the methods described herein permit the incorporation of unsaturation between carbon atoms 3 and 4 of the pyrrolidinyl group. While inclusion of such unsaturation alters the nomenclature of the resulting compounds to 3-pyrrolinyl, they are nevertheless encompassed within the scope of the term "pyrrolidinyl" for the purposes of this disclosure. When the ring contains such unsaturatation, the pyrrolidinyl group can be depicted as follows:

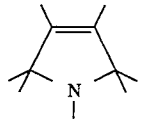

The term "a compound having at least one imine group with a methine or methylene hydrogen atom a to the nitrogen atom of the imine group" refers to any compound which structure comprises a

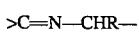

>C=N—CHR— group covalently attached to the compound wherein R is any substituent which does not form an unsaturated moiety with the CH group so that the CHR group defines a methine or methylene group.

The term "a complementary compound (group or moiety) having at least one site of carbon-carbon unsaturation" refers to those compounds, groups and moieties having carbon-carbon unsaturation which are reactive with azomethine ylides to form pyrrolidinyl compounds. Such complementary compounds, groups and moieties preferably employ an activating group to facilitate reaction with the azomethine ylide and one group of preferred activating groups is an electron withdrawing substituent or group which is preferably covalently attached to at least one of the unsaturated carbon atoms of the complementary compound, group or moieties. Suitable complementary compounds having at least one site of carbon-carbon unsaturation which contain an electron withdrawing group include, by way of example only, acrylic acid, acrolein, methacrylic acid, a-cyanoacrylic acid, acrylonitrile, fumaric acid, maleic acid, maleic anhydride, maleimide, N-substituted maleimide, acrylonitrile, acetylene dicarboxylic acid, isocrotonoic acid, crotononitrile, as well as esters of any of the recited carboxylic acids, and the like. Particular preferred complementary compounds having at least one site of carbon-carbon unsaturation include, by way of example, dimethyl maleate, dimethyl fumurate, methyl acrylate, methyl methacrylate, phenyl acrylate, ethyl acrylate, and acrylonitrile.

Preferred complementary groups or moieties having at least one site of carbon-carbon unsaturation include those derived from the compounds recited above but which are covalently attached to a larger molecule, e.g., a —CH═CH—CN group, etc.

As noted above, the carbon-carbon unsaturation includes both ethylenic unsaturation (i.e., >C═C<) and acetylenic unsaturation (i.e., —C≡C—). Use of a complementary compound, group or moiety having ethylenic unsaturation results in a saturated pyrrolidinyl group whereas the use of a complementary compound, group or moiety having acetylenic unsaturated results in a pyrrolidinyl compound having ethylenic unsaturation between carbon atoms 3 and 4 of the pyrrolidinyl group (i.e., a pyrrolinyl group).

The particular complementary compound having carbon-carbon unsaturation employed in the methods described herein is not critical.

Methods for Preparing Groups on Solid Supports

The synthesis of a pyrrolidinyl group on the solid support is effected by reaction of an azomethine ylide with a complementary compound having carbon-carbon unsaturation. In turn, an azomethine ylide is generated from an azomethine ylide precursor compound by methods well known in the art. Surprisingly, it has been found that these known methods can be conducted on solid supports thereby providing methods for generating libraries of compounds containing pyrrolidinyl groups on solid supports.

Figure 1:
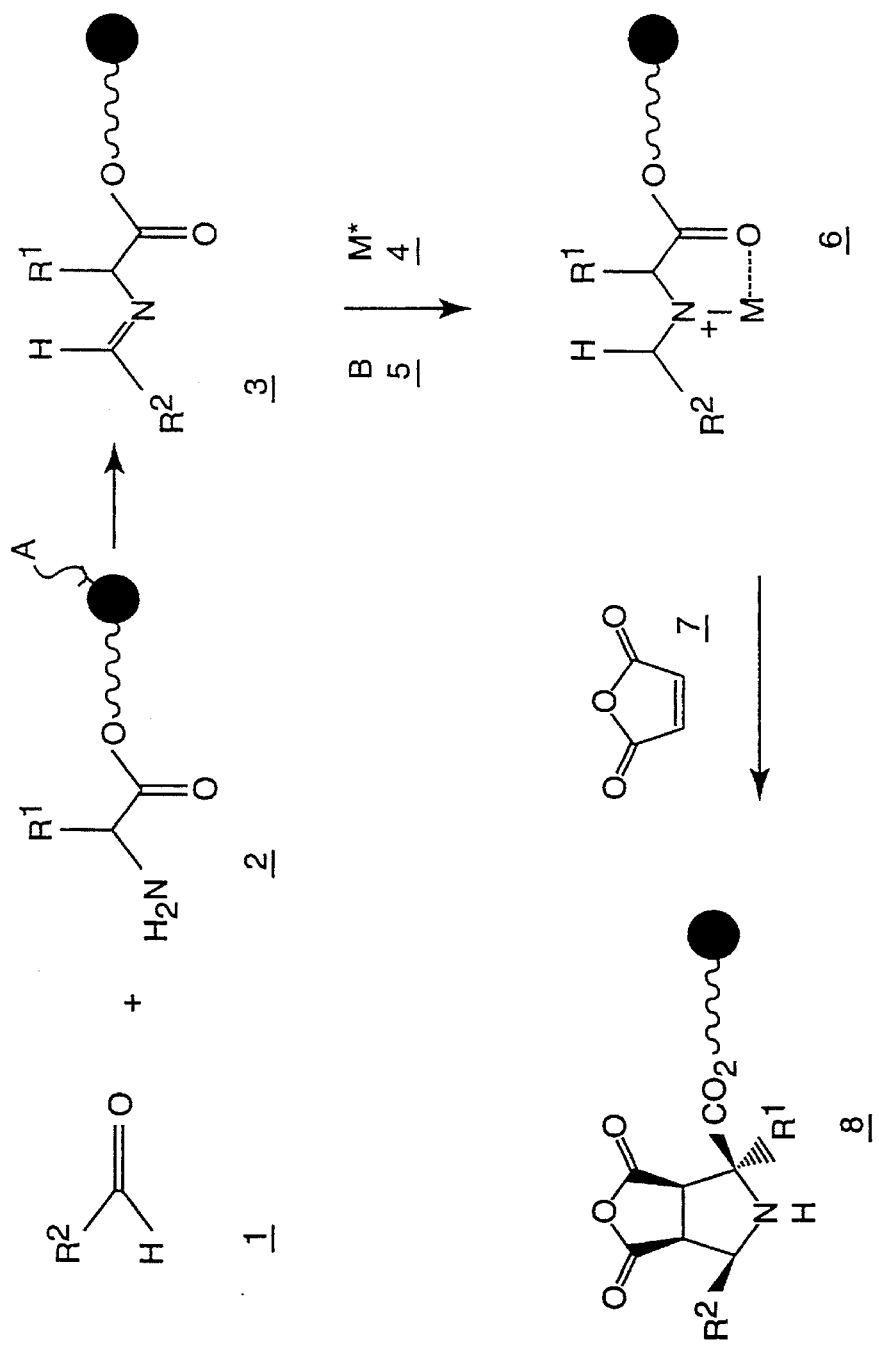
FIG. 1 illustrates the synthesis of an azomethine ylide precursor 3 on a solid support A, conversion of precursor 3 to azomethine ylide 6 and subsequent formation of pyrrolidinyl group 8.

The generation of an azomethine ylide from a precursor molecule is well documented in the art.[14–31] However, one particularly preferred method is the treatment of an imine having a methine or methylene hydrogen atom alpha to the nitrogen atom of the imine group with a base (B) of sufficient basicity to extract this methine or methylene hydrogen atom. Specifically, as illustrated in FIG. 1, imine 3 is treated with base 5 to provide for azomethine ylide 6. The resulting azomethine ylide 6 is reacted with a complementary compound having carbon-carbon unsaturation which, in FIG. 1, is illustrated with maleic anhydride 7 to provide for pyrrolidinyl compound 8.

Each procedure (formation of the azomethine ylide and reaction of this ylide with the complementary compound having carbon-carbon unsaturation) for this reaction is preferably conducted in a single reaction medium. The first procedure for this reaction is conducted in an inert solvent with a stoichiometric or excess amount of base 5 relative to imine 3. Although the choice of solvent may effect the stereoisomeric product distribution, the particular solvent employed is not critical. Suitable solvents include, by way of example only, acetonitrile, dimethylformamide, tetrahydrofuran and the like. A particularly preferred solvent is trimethyl orthoformate.

Likewise, the particular base employed is not critical and is selected relative only to its ability to extract the methine or methylene hydrogen atom thereby generating the azomethine ylide and to promote the formation of the cycloadduct rather than the cycloadduct.[32] Suitable bases include, by way of example only, triethylamine, diazabicyclo[4.3.0]undecene, pyridine, diazabicyclo[2.2.2]octane,n-butyllithium, lithium diisopropylamine, and the like.

The reaction is optionally, but preferably, conducted in the presence of at least an approximate stoichiometric amount of a Lewis acid 4 which facilitates reaction completion by enhancing the acidity of the methine or methylene hydrogen atom. Additionally, when a carbonyl group is β to the nitrogen atom of the imine (as depicted in compounds 3 and 6 of FIG. 1), the metallic cation of the Lewis acid chelates with this carbonyl group thereby increasing the acidity of the methine or methylene hydrogen interposed between the nitrogen atom of the imine and the carbon atom of the carbonyl group. In turn, this increase in acidity permits the use of milder bases to effect extraction of the methine hydrogen atom.

Suitable Lewis acids are well known in the art and the particular Lewis acid employed is not critical. Suitable Lewis acids include, but are not limited to, silver(I) nitrate, silver(I) carbonate, lithium chloride, lithium bromide, zinc(II) chloride, titanium(IV) chloride, aluminum(III) chloride, titanium(IV) isopropoxide, zirconium(IV) chloride, palladium(II) chloride, cobalt(II) chloride, and lanthanum(III) triflate. In one preferred embodiment, the Lewis acid is selected from the group consisting of silver(I) nitrate, silver(I) carbonate, lithium chloride, lithium bromide, and the like which are depicted as $M^+$ in FIG. 1.

The choice and concentration of Lewis acid (as well as the nature of the resin support) may effect the selectivity of the cycloaddition reaction. For example, with Lewis acids capable of chelation, endo-selective cycloadditions to the W-configured (syn) azomethine ylides typically will predominate, presumably due to chelation control in the transition states.[1] Poorer selectivity is seen in cycloadditions to complementary compounds having carbon-carbon unsaturation, but lacking a carbonyl substituent (e.g., acrylonitrile). Importantly, the product distribution is highly reproducible for any given set of conditions. Generally, the reactions were performed using TentaGel supports with 1M silver (I) nitrate in acetonitrile or 2M lithium bromide in THF.

The complementary compound having carbon-carbon unsaturation is preferably added to this reaction medium prior to initiation of the reaction so that upon formation, the azomethine ylide is in situ converted to pyrrolidinyl compound 8.

The reaction conditions are otherwise not critical and, preferably, the reaction is conducted at from about 0° C. to about 100° C. for from about 0.5 to about 24 hours.

For some applications, one may desire a "support-free" or "soluble" library of molecules. Soluble molecules, both tagged and untagged, can be useful for a variety of purposes, including assaying the activity of a compound and structural analysis. The generation of soluble molecular libraries, both tagged and untagged, and the solubilization of compounds, both tagged and untagged, synthesized on a solid support can be accomplished by techniques known in the art, using for example, the cleavable linking arms described in U.S. Ser. No. 978,940, filed Nov. 19, 1992, now abandoned, incorporated herein by reference. Typically, TFA (the concentration (%) TFA often will vary according to the type of linker or linking arm employed) will be used to cleave the pyrrolidines from the resin.

The resulting pyrrolidinyl compound 8 is recovered by conventional methods, i.e., filtration, centrifugation, etc. Confirmation that the resin (i.e., solid support) contains the desired pyrrolidinyl compound can be accomplished by cleaving the pyrrolidinyl compound from a small portion of the treated resins (if a cleavable linking arm is employed) and subjecting this product to conventional analysis, e.g., nuclear magnetic resonance spectroscopy ($^1H$, $^{13}C$, etc.), high performance liquid chromatography, and the like.

High-resolution gel phase $^{13}C$ nuclear magnetic resonance (NMR) spectroscopy can be used to monitor the progress of a reaction and/or to identify the product. Changes in hybridization and electron density can be easily monitored using this technique with little interference from solvent or other non-labeled sites.

Resins and linkers which do not have absorbances in the regions of interest should be used. Suitable resins for this use include those illustrated in FIGS. 2B–2D attached. Preferably, a polystyrene resin, such as TentaGel, and a polyethyleneglycol (PEG) linker, is used. Polystyrene resins tend to be $^{13}C$-invisible and the linker often will exhibit a single sharp resonance at about 70 ppm.

A $^{13}C$ label typically is incorporated into at least one of the components or building blocks. The label typically will be incorporated into the amine or carbonyl component because of the commercial availability of these compounds. However, one of skill in the art will readily appreciate that the other components could also be labeled. For example, the aldehyde can be $^{13}C$ labeled and then treated with a mixture of resin-bound (TentaGel™ resin with a PEG-linker) amino acids to yield the corresponding Schiff bases. When benzaldehyde which has been labeled at the carbonyl carbon (Ph$^{13}$CHO) is used, the $^{13}C$ NMR exhibits a singlet resonance for each of the different imine carbon around 160–165 ppm. Upon cycloaddition, these resonances are replaced by resonances for the C-5 of the pyrrolidine ring at about 60–70 ppm.

Other means for forming azomethine ylides from suitable azomethine ylide precursors are well known in the art and include by way of example, ring opening of aziridines[1]. The particular azomethine ylide precursor and the method employed to convert this precursor to the azomethine ylide employed is not critical. For example, suitable azomethine ylide precursors can employ a silyl group as disclosed by Tsuge, et al.[1] which can be converted to the azomethine ylide without the need for a base. Such precursors are of particular value when basic conditions are to be avoided.

FIG. 1 further illustrates the formation of imine compound 3, which serves as an azomethine ylide precursor, by conventional methods from a suitable aldehyde 1 (ketones can also be used) and amine 2. The reaction is conducted in an inert solvent under conditions which eliminate water thereby forming imine 3. Preferred inert solvents include those that will form an azeotrope with water so that water generated during reaction can be readily removed. Such preferred solvents include by way of example, benzene, toluene, etc. Preferred reaction conditions include the use benzene or benzene/triethylamine under refluxing conditions; the use of benzene/Dean Stark trap or 4A molecular sieves under refluxing conditions; the use of methanol or methanol/triethylamine; the use of tetrahydrofuran/$Si(OC_2H_5)_4$/1% $H_2SO_4$; and the use of trimethyl orthoformate. Particularly preferred is the use of neat trimethyl orthoformate as the solvent/dehydrating agent.

FIG. 1 illustrates formation of imine 3 from amine 2 attached to a solid support which is reacted with soluble aldehyde 1. It is understood, however, that aldehyde 1 (or a ketone) can be covalently attached to the solid support and that amine 2 is in soluble form (i.e., not attached to the solid support). In both cases, the resulting imine is covalently bound to the solid support.

It is further understood, however, that the complementary compound having at least one site of carbon-carbon unsaturation can be covalently attached to the solid support which can then be reacted with a soluble azomethine ylide (not attached to the support) to provide for a pyrrolidinyl group covalently attached to the support. In such an embodiments, this reaction is conducted in the manner to that described above.

In the particular embodiment illustrated in FIG. 1, the amine 2 is an amino acid wherein the acid group is attached to the solid support via an ester bond. Such amino acids form a preferred subclass of suitable amines because these amino acids will result in a carbonyl group β to the resulting imine nitrogen. Suitable amino acids include all naturally occurring as well as synthetic amino acids including, by way of example, the D-amino acids of naturally occurring L-amino acids. The amino acid can be the N-terminal amino acid of a peptide bound to the solid support which, after formation of the pyrrolidinyl group can optionally be further reacted under conventional peptide synthetic conditions through an N—H group of the pyrrolidinyl group to extend the peptide length.

Alternatively, the >NH group of the pyrrolidinyl compound can be acylated via conventional means to provide for acylated pyrrolidinyl compounds. A particularly preferred class of acylating reagents comprise the formula $HSCH_2CHR^3C(O)$— which, when reacted with the pyrrolidinyl compound form a class of Captopril™ derivatives which are then screened for anti-hypertensive activity as described in greater detail below. $R^3$ being a substituent having the same values as recited above for the substituents listed for the pyrrolidinyl group. Typically, the acylating reagent will comprise an acyl halide having the formula $HSCH_2CHR^3C(O)X$ wherein X is bromine or chlorine. One of skill in the art will readily appreciate that other compounds having activated carboxyl groups can also be used as the acylating reagent.

In another embodiment, the aldehyde 1 (or ketone) can comprise ethylenic unsaturation so that the resulting imine can undergo internal cyclization via the ethylenic unsaturation on the aldehyde. Suitable examples of such aldehydes include those of formula I below:

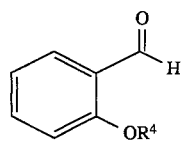

where $R^4$ is —$(CH_2)_n$—CH=$CH_2$(n=1 or 2), —$CH_2$—CH=CH—$CO_2CH_3$, and —$CH_2C$≡CH.

The methods of the present invention are readily automated using technology presently available for binding and reacting monomers to form polymer chains and removing the byproducts of those reactions. Moreover, the methods described herein are amenable to the simultaneous production of a variety of different pyrrolidines.

An apparatus capable of preparing arrays of pyrrolidines is described in U.S. patent application Ser. No. 08/149,675, filed Nov. 2, 1993, incorporated herein by reference. Such an instrument is capable of performing up to 100 or more parallel reactions simultaneously by distributing the reaction mixture or slurry of synthesis solid supports, under programmable control, to the various channels for pooling, mixing, and redistribution.

Another apparatus capable of preparing arrays according to the methods described herein is described in association with the synthesis of peptides in Geysen et al., *J. Immun. Methods* (1987) 102:259–274, incorporated herein by reference for all purposes. In brief, this method utilizes a solid support having a plurality of pins or other extensions. The pins are each inserted simultaneously into individual reagent containers in tray. Although in a common embodiment, an array of 96 pins/containers is utilized, it will be recognized that in other embodiments a larger array of such pins/containers will be provided. Each tray is filled with a particular reagent for coupling in a particular chemical reaction on an individual pin. Accordingly, the trays will often contain different reagents. Since the chemistry disclosed herein has been established such that a relatively similar set of reaction conditions may be utilized to perform each of the reactions, it becomes possible to conduct multiple chemical coupling steps simultaneously.

Other instruments amenable for use with the methods described herein are commercially available. For example, robotic systems, such as that available from Advanced Chemtech, and other non-pin based instruments can be utilized.

Method for Producing Large Synthetic Libraries of Pyrrolidinyl Compounds

The above described synthetic methods can be incorporated into one or more reaction procedures in the stochastic methods described in International Patent Application Publication No. 93/06121 to prepare synthetic libraries of pyrrolidinyl compounds on solid supports. This application is incorporated herein by reference in its entirety. In such libraries, each solid support will preferably contain a single compound which compound is different to the compounds found on the other solid supports but each compound will also comprise a pyrrolidinyl compound.

The methods described above may be used to prepare and screen large numbers of compounds, in the hundreds, the thousands and even the ten thousands in a reasonable period of time. Synthesis may be combined with screening in various different ways to screen compounds in unusually large libraries. Preferably, the techniques described above are used to synthesize more than 2, preferably more than 5, preferably more than 10, more preferably more than 50, more preferably more than 100, and more preferably more than 1,000 different molecules simultaneously.

It is understood, however, that the term "single compound" as used herein includes different regio and stereo isomers of that compound. Also, the term "single compound" does not mean that only one copy of that compound is attached to each support. Rather, multiple copies of that compound can be included on the support.

In general, such methods comprise apportioning the supports comprising a covalently bound azomethine ylide precursor or a complementary compound having at least one site of carbon-carbon unsaturation among a plurality of reaction vessels; exposing the supports in each reaction vessel under conditions wherein the azomethine ylide precursor or the complementary compound is converted to a pyrrolidinyl group wherein said pyrrolidinyl group is different for each of the reaction vessels; and optionally, pooling the supports.

In one embodiment, the azomethine ylide precursor is converted to a pyrrolidinyl group by first converting the ylide precursor to an azomethine ylide followed by reaction of the azomethine ylide with a complementary compound having at least one site of carbon-carbon unsaturation.

In another embodiment, the complementary group containing at least one site of carbon-carbon unsaturation is converted to a pyrrolidinyl group by reaction with an azomethine ylide.

In a preferred aspect of this embodiment, each solid support is tagged with an identifier tag that can be easily decoded to report the compounds formed on the solid support. The tag can be directly attached either to the solid support or the tag can be included on the compound itself. In this latter embodiment, cleavage of the compound from the solid support will still permit identification of the compound. Each of these embodiments is disclosed in International Patent Application Publication No. WO 93/06121. Alternatively, a portion of the same compounds attached to a single support is cleaved and subjected to mass spectroscopy, nuclear magnetic resonance spectroscopy and/or other forms of direct structural analysis so as to identify the compound on the support.

Still another method for incorporating a tag with the solid support is disclosed in U.S. patent application Ser. No. 08/146,886, filed Nov. 2, 1994, and entitled "METHOD OF SYNTHESIZING DIVERSE COLLECTIONS OF COMPOUNDS" which application is incorporated herein by reference in its entirety.

In still another embodiment, the pyrrolidinyl group can be incorporated into each compound in a library of different compounds all of which are covalently linked to the same solid support in the manner described in U.S. Pat. No. 5,143,854. Such a library of different compounds can be simultaneously screened for receptor binding or some other activity. U.S. Pat. No. 5,143,854 is incorporated herein by reference in its entirety.

Additionally, libraries of compounds attached to solid supports can be used for a variety of additional uses as set forth in International Patent Application Publication No. WO 93/06121.

Assays and Other Screening Methods

Since a wide array of building blocks are readily available, the synthesis technique herein results in an array of immobilized materials which are at known locations on the solid support or in a soluble format and may be effectively used in screening studies to identify compounds having biological or pharmaceutical activity.

For example, a screening assay to determine which of the synthesized materials show significant affinity for a receptor or receptors of interest can be performed. Receptor affinity can be studied by exposing the solid support to the receptor or receptors of interest, and determining where the receptor has bound to the solid support. In some embodiments, the location of the receptor on the solid support may be conveniently located by labeling the receptor with an radioactive or fluorescent label, and scanning the surface of the solid support for the presence of the receptor. In some embodiments, the receptor of interest may be unlabeled, but later exposed to a second receptor that is labeled and known to be complementary to the receptor of interest. The receptor will bind to the molecules that are complementary to the receptor while it will not bind to other molecules on the solid support. Accordingly, the present method provides an effective way to identify ligands that are complementary to a receptor.

In a particularly preferred embodiment, the solid support comprises beads and the receptor is fluorescently or radioactively labeled. Thereafter, one or more beads are identified that exhibit significant levels of, for example, fluorescence using one of a variety of techniques. For example, in a preferred embodiment, fluorescence activated cell sorting (FACS) is used to select for those beads having selected levels of fluorescence. In another embodiment, mechanical separation under a microscope is utilized. The identity of the molecule on the surface of such separated beads is then identified using, for example, NMR, mass spectrometry, or the like.

In alternative embodiments the identity of the molecule that is complementary to the receptor is determined with respect to the "bin" or container in which the labeled receptor is located. For example, by exposing the molecules in the various containers to the labeled receptor, the identity of one terminal portion of the molecule may be identified. For example, if fluorescence is noted after exposure to the molecules in the first container, but not in the second or third containers, it is readily determined that the molecule that produces a complementary receptor is having the building block introduced in the first container as opposed to those molecules having the building blocks introduced in the second or third containers. Thereafter, one will synthesize all of the molecules having the "active" building block in separate containers. The identity of the other active portions of the molecule can then be determined by identifying where receptor binding is located among these molecules.

One can also employ molecular libraries to useful effect in novel assays of the invention in which a ligand is solubilized in either tagged or untagged form prior to binding to a receptor of interest. For screening very large libraries of soluble tagged libraries, one preferably employs affinity chromatography under conditions of weak affinity.

Soluble molecules can also be screened using an immobilized receptor. After contacting the molecules with the immobilized receptor, and washing away non-specifically bound molecules, bound molecules are released from the receptor by any of a wide variety of methods. The tags, if present, are optionally amplified and then examined and decoded to identify the structure of the molecules that bind specifically to the receptor. A tagged molecule in solution can be assayed using a receptor immobilized by attachment to a bead, for example, by a competition assay with a fluorescently labeled to ligand. The beads bearing immobilized receptors can be recovered and the sorted using FACS to identify positives (diminished fluorescence caused by the library molecule competing with the labeled ligand).

The soluble molecules of the library can be synthesized on a solid support and then cleaved prior to assay. In one embodiment, microscopic beads of a molecular library are placed in very small individual compartments or wells that have been "nanofabricated" in a silicon or other suitable surface. Beads are loaded into the wells by dispersing them in a volume of loading buffer sufficient to produce an average of one bead per well. In another embodiment, the solution of beads is placed in a reservoir above the wells and the beads are allowed to settle into the wells. Cleavage of the molecules from the beads may be accomplished using chemical or thermal systems, but a photocleavable system is preferred. The molecules of interest can be cleaved from the beads to produce either untagged molecules in solution (the tag remaining attached to the bad) or tagged molecules in solution. In either event, the molecules of interest are cleaved from the beads but remain contained within the compartment along with the bead and the identifier tag(s).

In another embodiment, relatively large tagged beads, from which the molecules of interest are cleaved in a series of reactions, are used. In this method, the beads are 50 to 500 μm in diameter, with capacities equivalent to 100 to 500 pmol of molecule per bead. The library is divided into about 100 pools, each containing about 100,000 beads. A certain percentage, about 25% of the molecule of interest is cleaved from the pool.

The cleaved pool is then tested in a competition or functional assay. One identifies the pool with the highest activity and then retrieves the remainder of the original pool and aliquots the remainder into 100 pools of about 1000 beads per pool. The process is repeated until one has a single bead, from which one reads the tag and identifies the compound of interest.

Techniques are also available which allow for the cleavage of a portion of the support-bound pyrrolidines while leaving the remainder of the support-bound molecules intact. In addition to the assay procedures described below, these techniques will find use in the structural analysis and identification of the pyrrolidines. Specifically, a library of pyrrolidines can be assayed using procedures known in the art and a first population of the library is selected as having desirable characteristics. This first population of these support-bound molecules can be subjected to cleavage conditions such that only a portion of the molecules are cleaved from the support. The cleaved material can be isolated and analyzed using conventional techniques, preferably mass spectroscopy. As many, if not all, of the members of the library will have distinctive molecular weights or other physical characteristics, the identity of the desirable molecules can be ascertained from the analyses. Thus, in certain circumstances, it will not be necessary to "tag" the molecules. The pyrrolidines, by virtue of their molecular weight characteristics, can serve as "self-tags".

The Identification of ACE Inhibitors

Figure 3:
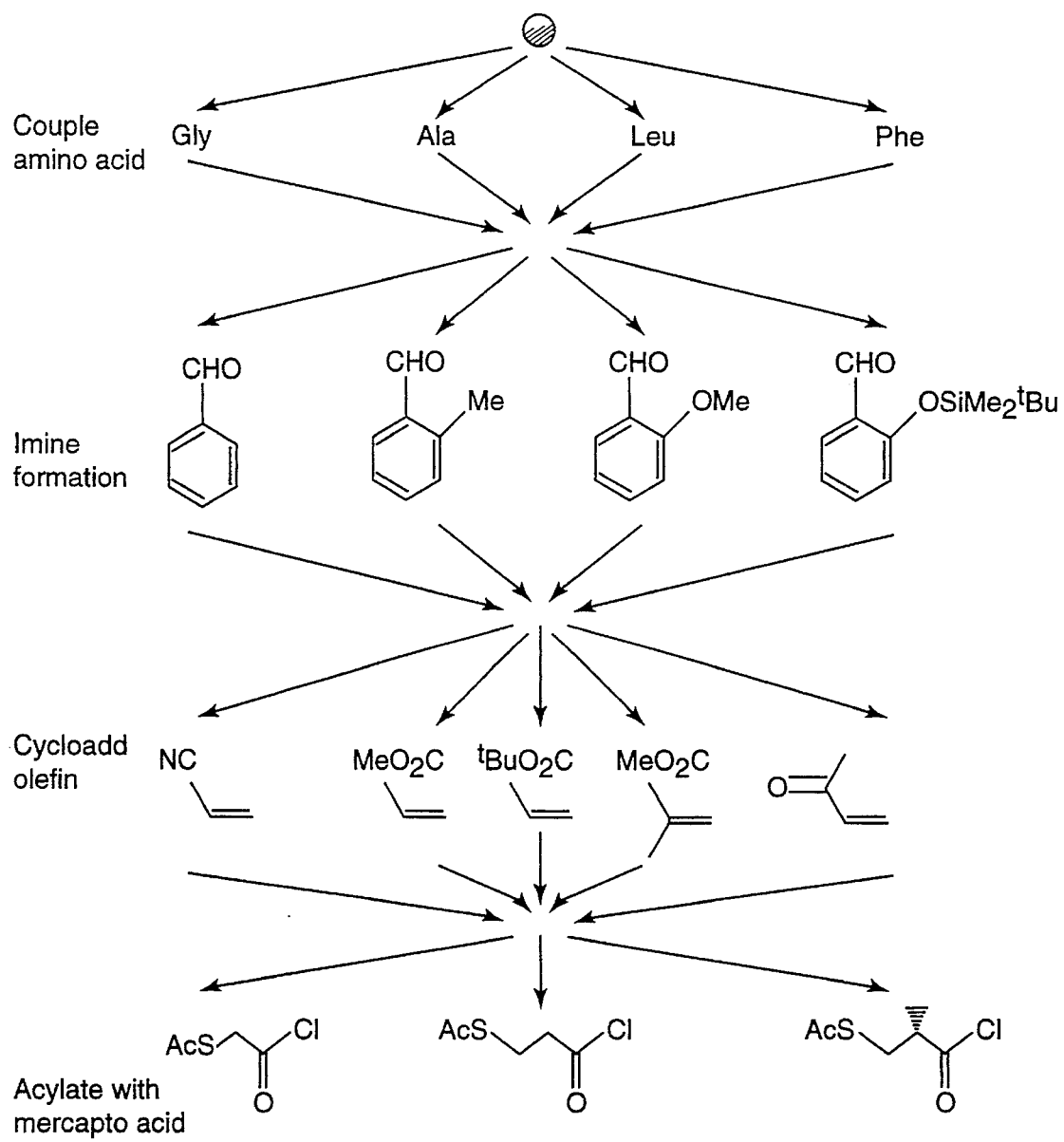
FIG. 3 illustrates a split/pool combinatorial synthesis approach capable of producing a library of mercaptoacyl proline derivatives from amino acid, aldehyde, olefin, and mercapto acid building blocks.
Figure 4A:
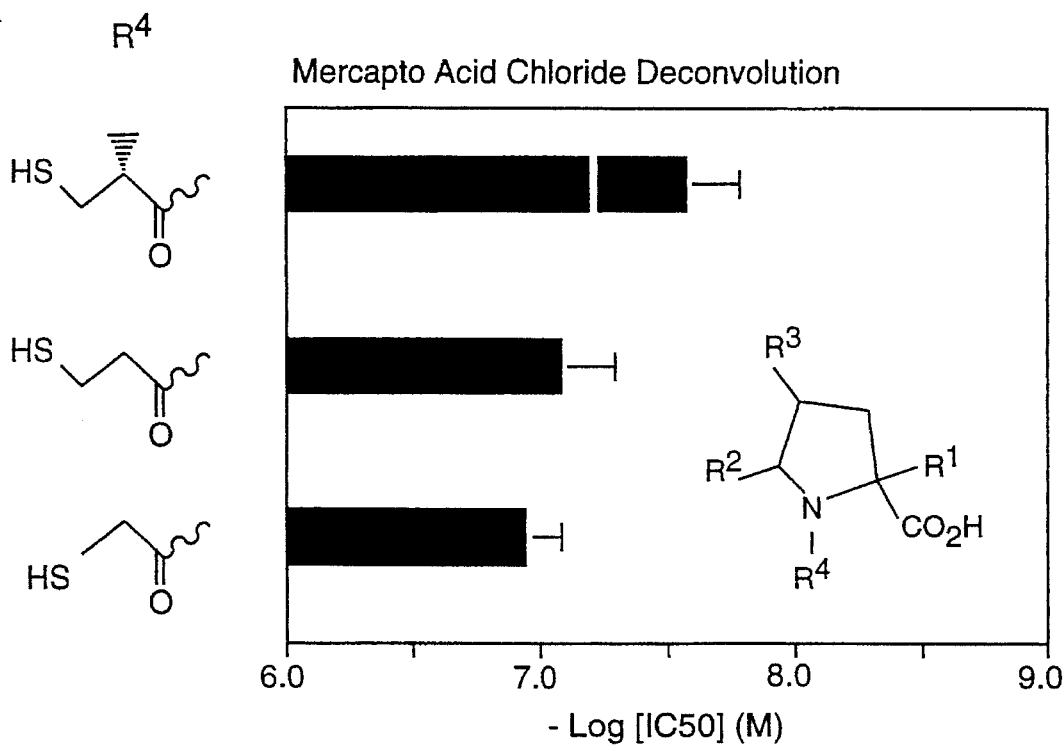
FIG. 4 illustrates the identification of a potent ACE inhibitor using deconvolution analysis. The inhibitory activity of pools of decreasing complexity ((a)–(d)) produced by iterative resynthesis is shown, where $IC_{50}$ refers to the total concentration of the pool (determined as free thiol by Ellman assay) giving 50% inhibition of hydrolysis of Hip-His-Leu (1 mM) by rabbit kidney ACE (2 nm).
Figure 4B:
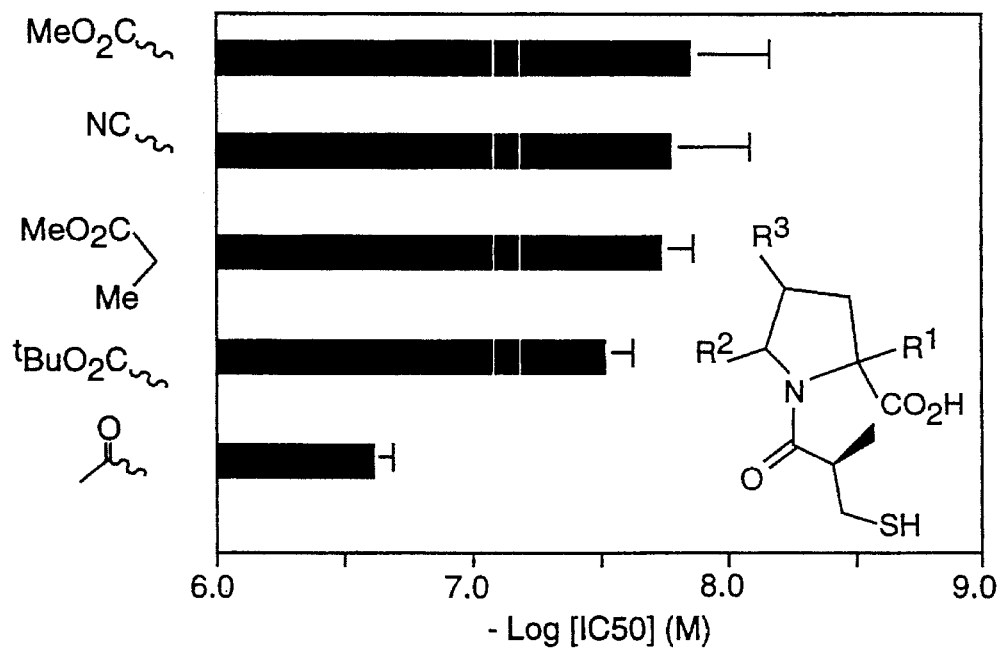
Figure 4C:
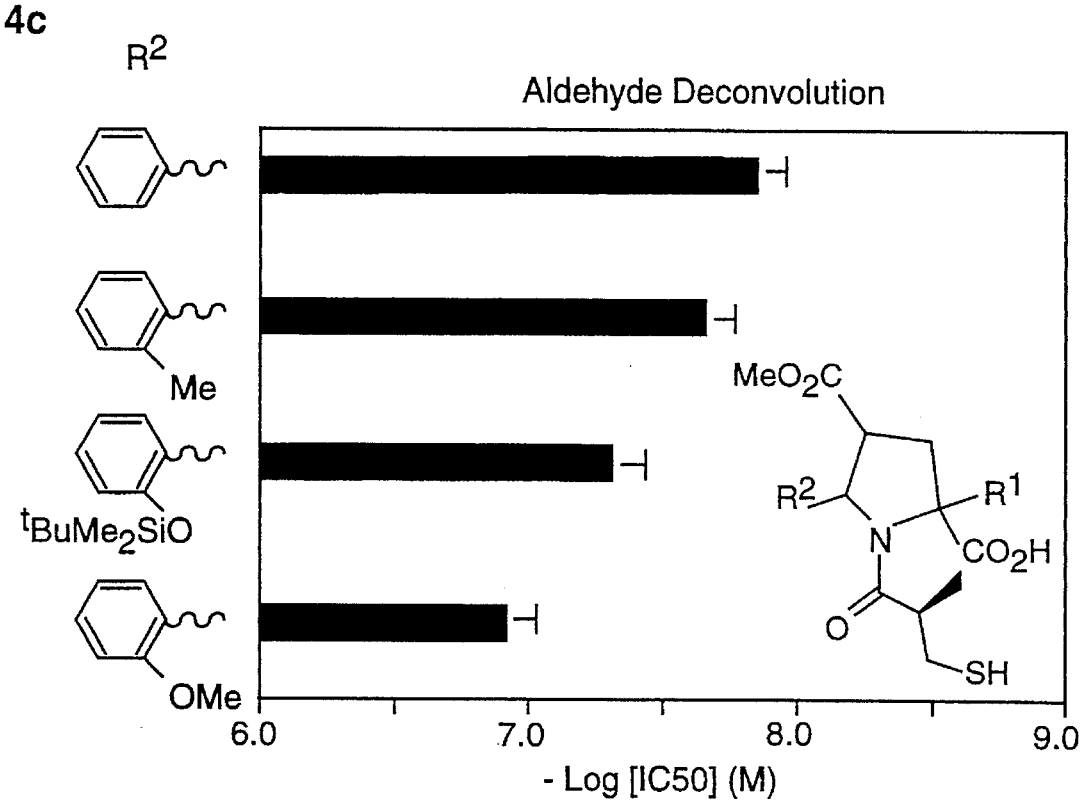
Figure 4D:
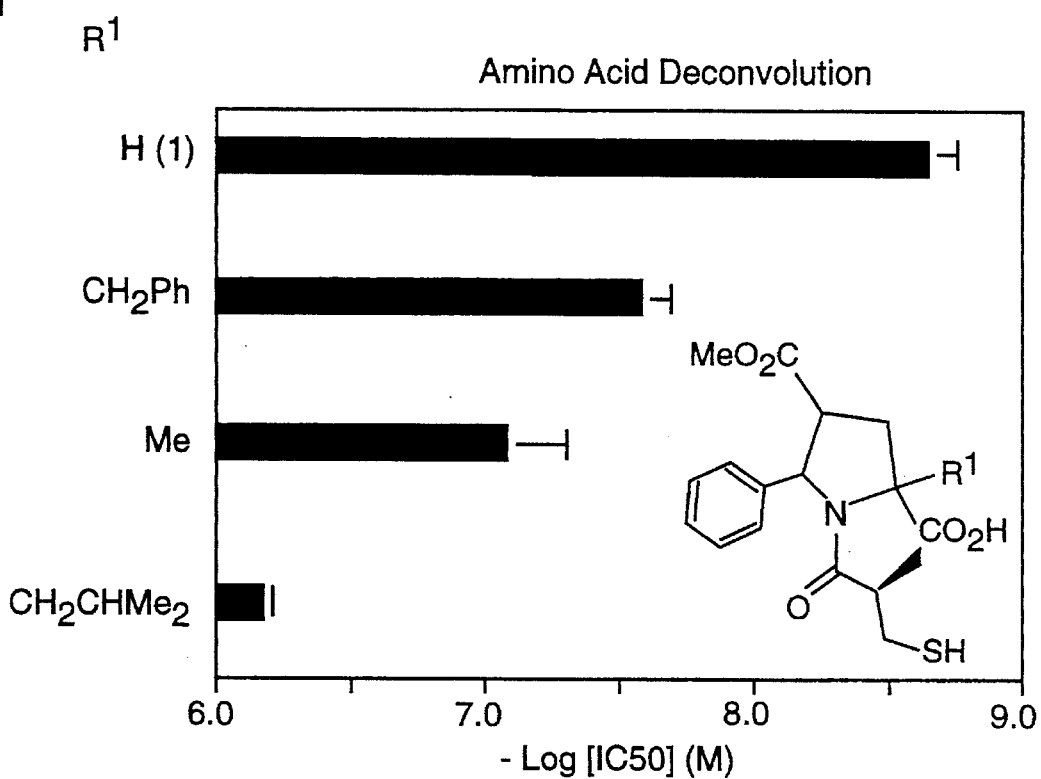

Functionalized prolines and proline analogs are frequently found as the C-terminal residue in numerous ACE inhibitors. Using the methods described herein, a library of prolines and proline analogs has been prepared. The library was formed by the split synthesis method[35], using four amino acids, four aldehydes, five olefins, and three mercaptoacyl chlorides as shown in FIG. 3 below. The 240 possible building block combinations were expected to yield more than 480 distinct products since the cycloaddition chemistry does not proceed with complete regio- and stereospecificity, and pyrrolidines derived from reaction of achiral aldehydes and olefins with homochiral amino acids are racemic as the α-carbon stereochemistry may be scrambled in the metallodipole intermediate. After cleavage from the resin (10% TFA in dichloromethane) and deacetylation of the protected mercaptoacyl proline products with ethylenediamine, the library was screened for in vitro inhibition of ACE[33] as soluble compound pools through four iterations of assay and sub-library resynthesis. At each step of this deconvolution analysis, the building block affording the most inhibitory pool was selected for the subsequent sub-library resynthesis. The results are summarized in FIG. 4.

Figure 5:
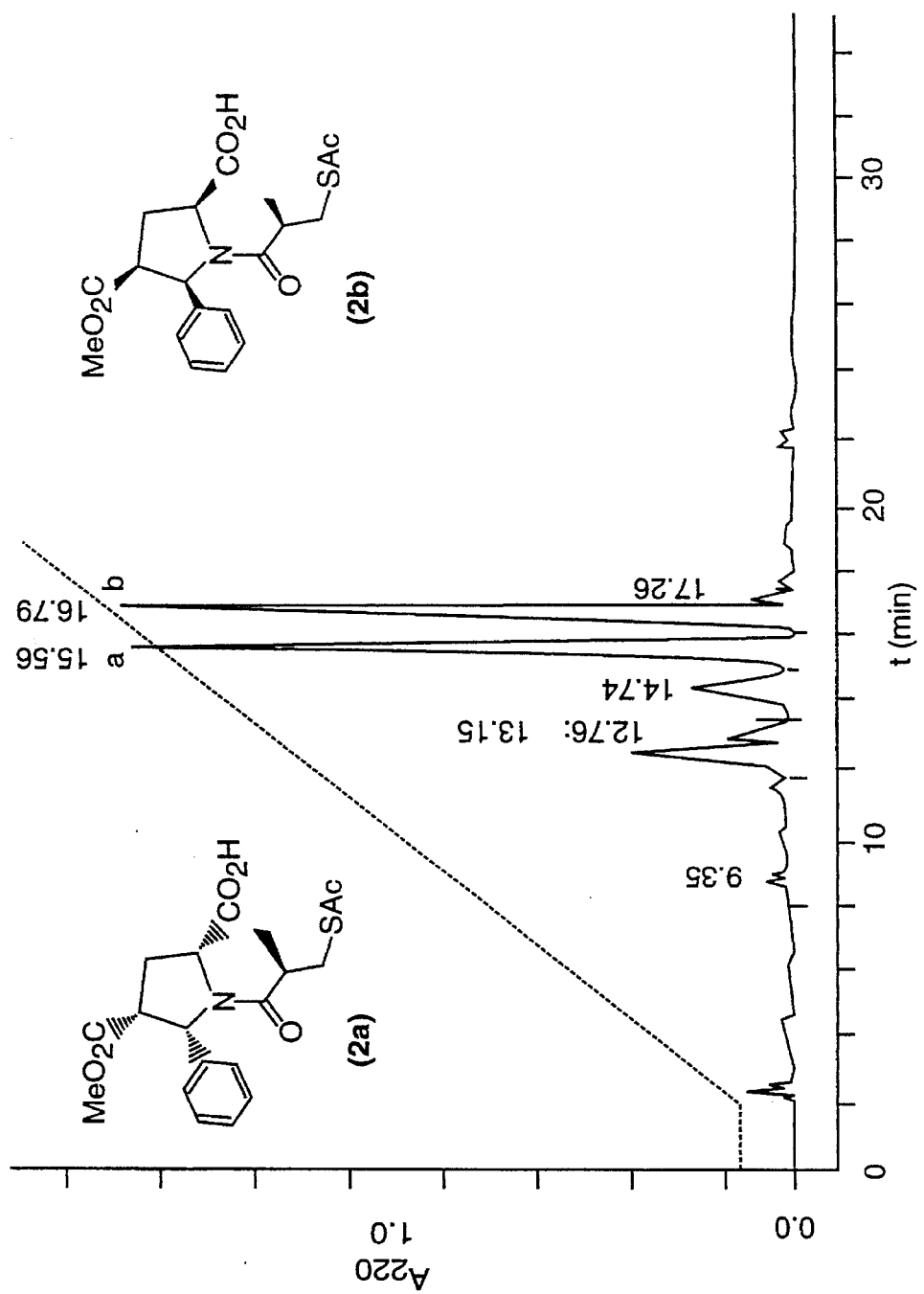
FIG. 5 depicts a HPLC analysis of ACE-inhibitory mercaptoacyl proline precursors (compounds 10 and 11) from preparative solid-phase synthesis.

This strategy led to the identification of 1-(3'-thio-2'(S)-methyl-1'-oxopropyl)-5-phenyl-2,4-pyrrolidinedicarboxy acid 4-methyl ester as a potent ACE inhibitor. An HPLC analysis of an independent preparative solid-phase synthesis of the S-acetylated precursor (see FIG. 5) indicated that the crude product predominantly consisted of an equimolar mixture of 2 components, characterized as diastereomers derived from a racemic proline intermediate. These isomers were purified and the relative stereochemical relationships between the 2, 4, and 5-pyrrolidine substituents (all syn), established by correlation with literature $^1$H NMR data, confirming that the proline ring arose through an endocycloaddition reaction.

Biological assay of the individual diastereomers after deacetylation facilitated assignment of the absolute configurations at C-2 of the prolines in these compounds. The earlier eluting isomer displayed very weak ACE-inhibitory activity ($K_i$>1 μM), and on the basis of extensive structure-activity date[36] is consistent with a 2-R configuration. By contrast, the later eluting isomer provided an exceedingly potent ACE inhibitor ($K_i$~160 pm), approximately 3-fold more active than captopril in this assay[37] and among the highest affinity thiol-containing ACE inhibitors yet described.

These ACE inhibitors are useful in treating hypertension and other related disorders and can be combined with suitable adjuvants and the like and formulated into pharmaceutical preparations using techniques known in the art. See, U.S. Pat. No. 5,164,407, which is incorporated herein by reference.

EXAMPLES

The following examples are set forth to illustrate the claimed invention and are not to be construed as a limitation thereof.

Unless otherwise stated, all temperatures are in degrees Celsius (°C.). Also, in these examples, unless otherwise defined below, the abbreviations employed have their generally accepted meaning:

```
app d = apparent doublet
app q = apparent quartet
app t = apparent triplet
Ar = phenyl
br s = broad singlet
d = doublet
dd = doublet of doublets
DMSO-d_6 = deutrated dimethyl sulfoxide
FMOC = fluorenylmethyl oxycarbonyl
1H-nmr = proton nuclear magnetic resonance
HPLC = high performance liquid chromatography
m = multiplet
MHz = megahertz
mL = milliliter
mmol = millimol
s = singlet
TFA = trifluoroacetic acid
```

Additionally the Sasrin resin described herein is commercially available from Bachem Biosciences and the TentaGel Ac resin, TentaGel PHB resin and TentaGel RAM resin are commercially available from Rapp Polymere, Tubigen, Germany. Each of these resins is depicted in FIGS. 2A–2D respectively.

Solid phase reactions were carried out at room temperature. Reagents were bought from Aldrich, Sigma, ICN, and Rapp Polymere and used without further purification. Concentration of solutions after workup was performed by reduced pressure rotary evaporation.

NMR spectra were obtained on a Varian Gemini 300 instrument with $CDCl_3$ as the solvent unless noted. $^1H$ NMR spectral data are reported as follows: chemical shifts relative to tetramethylsilane (0.00 ppm), multiplicity, coupling, and integration. Assignment of protons was aided by decoupling experiments. $^{13}C$ signals are reported in ppm relative to $CDCl_3$ (77.0 ppm). Infrared spectra were obtained on a Nicolet 120X instrument employing 3M disposable teflon cards. Data are reported as % transmittance.

High performance liquid chromatography was performed on a Beckman Gold Analytic 126 apparatus with a diode array detector model 168 at the wavelengths 220 nm and 280 nm. The column employed was an Econosphere C8 cartridge 250 mm×4.6 mm. Semi-preparative chromatography was performed on a Beckman 110B apparatus with a model 166 detector at the wavelength 220 nm. The column employed was a Waters RCM (25×10 cm).

Experimental

The following experimental outlines the general procedures employed in the examples below to prepare the pyrrolidine compounds depicted therein.

General solid phase condition for imine formation

Resin bound glycine FMOC (0.25 millimole (mmol) loading) is added to 10 milliliters (mL) of 20% piperidine in dimethyl formamide for one hour. The resin is filtered through a fritted funnel and washed with dimethyl formamide (3×10 mL) and methylene chloride (3×20 mL). To a 10 mL round bottom flask is added aldehyde (2.5 mmol) and the resin (0.25 mmol loading) in 8 mL of benzene. The solution is fitted with a Dean Stark trap and filled with benzene and subsequently refluxed mildly for one hour to two hours. The solution is filtered through a fritted glass filter and the residue is washed with benzene (3×10 mL) and methylene chloride (3×10 mL).

General solid phase condition for [2+3] cycloaddition with Silver(I)

To a 10 mL screw capped vial is added resin (0.125 mmol loading), olefin (1.5 mmol), and silver(I) nitrate (1.5 mmol) in approximately 5 mL of acetonitrile. To the solution is added triethyl amine (1.5 mmol) by syringe dropwise in a hood with the light off. The vial is very mildly agitated by a shaker table and the heterogeneous solution is observed to change colors from clear to black in two to four hours and a silver mirror is seen to be present after 8 to 12 hours. After 24 hours the resin solution is filtered through a fritted glass filter and washed with methylene chloride (5×10 mL). The resin is then added to a vial with 4 mL of trifluoroacetic acid in methylene chloride (% TFA varies according to the type of linker employed) for 30 minutes and subsequently filtered and washed with methylene chloride (3×5 mL). This procedure is repeated three times and the filtrates collected and rotary evaporated to dryness. The residue oil is analyzed by $^1H$ NMR and HPLC.

General solid phase condition for [2+3] Cycloaddition with Lithium(I)

To a 10 mL screw capped vial is added resin (0.125 mmol loading), olefin (1.5 mmol), and lithium(I) bromide (1.5 mmol) in approximately 5 mL of acetonitrile. To the solution is added triethyl amine (1.5 mmol) by syringe dropwise in a hood with the light off. The vial is agitated very mildly by a shaker table and the heterogeneous solution is observed to change colors from clear to cloudy in two to four hours. After 48 hours the resin solution is filtered through a fritted glass filter and washed with methylene chloride (5×10 mL). The resin is then added to a vial with 4 mL of trifluoroacetic acid in methylene chloride (% TFA varies according to the type of linker employed) for 30 minutes and subsequently filtered and washed with methylene chloride (3×5 mL). This procedure is repeated three times and the filtrates collected and rotary evaporated to dryness. The residue oil is analyzed by $H^1$ NMR and HPLC.

Example 1

By following the procedures set forth above, 4-cyano-5-phenyl-L-proline was prepared as shown below:

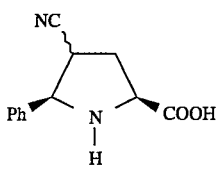

The aldehyde employed in this synthesis was benzaldehyde and the olefin was acrylonitrile. The support employed in this synthesis was Sasrin resin containing the cleavable linker depicted in FIG. 2A which, upon treatment with 25% trifluoroacetic acid (in methylene chloride), gave the soluble proline derivative. $^1H$-nmr data for this compound is as follows: ($D_2O$, 300 MHz) d 7.70–7.41 (m, 5H, ArH̲), 5.24 (d, 1H, ArCH̲), 5.15 (d, 1H, ArCH̲, epimer product at the cyano carbon), 4.72–4.63 (m, 1H, CHCO₂H), 4.27–4.14 (m, 1H, CHCN), 4.01–3.55 (m, 2H, CHCN, CHCO₂H epimer product at the cyano carbon), 3.11–2.84 (m, 2H, CH₂C HCO₂H including the epimer product), 2.16–2.10 (br s, 1H, NH). Yield 71.4%

Example 2

By following the procedures set forth above, 4-cyano-5-phenyl-L-proline was prepared as shown below:

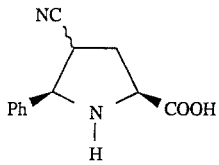

The aldehyde employed in this synthesis was benzaldehyde and the olefin was acrylonitrile. The support employed in this synthesis was TentaGel Ac resin containing the cleavable linker depicted in FIG. 2B which, upon treatment with 25% trifluoroacetic acid in methylene chloride, gave the soluble proline derivative. $^1$H-nmr data for this compound is as follows: $^1$H NMR (DMSO-$d_6$ 300 MHz) d 7.65–7.22 (m, 5H, ArH), 4.94 (app d 1H, ArCH, epimer product at the cyano carbon), 4.92(app d, 1H, ArCH), 4.65 (app t, 1H, CHCO₂H, epimer product at the cyano carbon), 4.50 (app t, 1H, CHCO₂H), 4.10(app q, 1H, CHCN), 3.81 (app q, 2H, CHCN, epimer product at the cyano carbon), 3.50 (br s due to glycine), 3.08–2.60 (m, 2H, CH₂CHCO₂H including the epimer product). Yield 40.0% (Ag), 20.7%(Li)

Example 3

By following the procedures set forth above, 4-cyano-5-phenyl-L-proline was prepared as shown below:

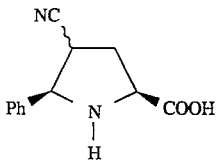

The aldehyde employed in this synthesis was benzaldehyde and the olefin was acrylonitrile. The support employed in this synthesis was TentaGel PHB resin containing the cleavable linker depicted in FIG. 2C which, upon treatment with 95% trifluoroacetic acid in methylene chloride, gave the soluble proline derivative. $^1$H-nmr data for this compound is as follows: $^1$H-nmr (DMSO-$d_6$ 300 MHz) d 7.65–7.38 (m, 5H, ArH), 4.89 (app d, 1H, ArCH), 4.87 (app d, 1H, ArCH, epimer product at the cyano carbon), 4.65(app t, 1H, CHCO₂H, epimer product at the cyano carbon), 4.48 (app t, 1H, CHCO₂H), 4.15–4.08 (m, 1H, CHCN), 3.81 (m, 2H, CHCN, epimer product at the cyano carbon), 3.50 (s due to glycine), 3.01–2.67 (m, 2H, CH₂CHCO₂H including the epimer product), 2.16–2.10 (br s, 1H, NH). Yield 12.6% (Ag), 8.0% (Li).

Example 4

By following the procedures set forth above, 2-amido-4-cyano- 5-phenyl-L-pyrrolidine was prepared as shown below:

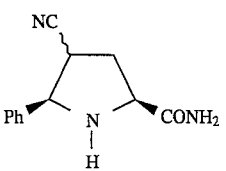

The aldehyde employed in this synthesis was benzaldehyde and the olefin was acrylonitrile. The support employed in this synthesis was TentaGel RAM resin containing the cleavable linker depicted in FIG. 2D which, upon treatment with 95% trifluoroacetic acid in methylene chloride, gave the soluble amide derivative. $^1$H-nmr data for this compound is as follows: (DMSO-$d_6$ 300 MHz) d 8.15 (br s, 2H, CON H₂), 7.98–7.45 (m, 5H,ArH), 5.02 (dd, 1H, CHCONH₂), 4.80 (d 1H, ArCH), 4.49(m, 1H, CHCN), 3.50 (s due to glycine), 2.85–2.40 (m, 2H, CH₂CHCONH₂). Yield 11.1% (Li)

Example 5

By following the procedures set forth above, 4-carboxymethyl-4-methyl-5-phenyl-L-proline was prepared as shown below:

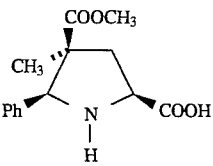

The aldehyde employed in this synthesis was benzaldehyde and the olefin was methyl methacrylate. The support employed in this synthesis was TentaGel AC resin which, upon treatment with 25% trifluoroacetic acid in methylene chloride, gave the soluble proline derivative. $^1$H-nmr data for this compounds is as follows: (DMSO-$d_6$ 300 MHz) d 7.47–7.20 (m, 5H, ArH), 4.79 (dd, 1H, CHCO₂H), 4.73 (d 1H, ArCH), 3.65 (s due to glycine), 3.49 (s, 3H, CO₂C H₃), 3.24–3.16 (m, 1H, NH), 2.86 (dd, 1H, CH₂CHCO₂H), 2.60 (dd, 1H, CH₂CHCO₂H), 1.43 (s,3H,C H₃). The regiochemistry of this compound is unclear. Yield 46.4% (Ag), 30.4% (Li)

Example 6

By following the procedures set forth above, 4-carboxymethyl- 4-methyl-5-phenyl-L-proline was prepared as shown below:

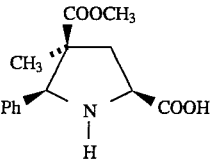

The aldehyde employed in this synthesis was benzaldehyde and the olefin was methyl methacrylate. The support employed in this synthesis was TentaGel PBH resin which, upon treatment with 95% trifluoroacetic acid in methylene chloride, gave the soluble proline derivative. $^1$H-nmr data for this compounds is as follows: (DMSO-$d_6$ 300 MHz) d 7.47–7.20 (m, 5H, ArH), 4.79 (dd, 1H, CHCO₂H), 4.73 (d 1H, ArCH), 3.65 (s due to glycine), 3.49 (s, 3H, CO₂C H₃), 3.24–3.16 (m, 1H, NH), 2.86 (dd, 1H, CH₂CHCO₂H), 2.60 (dd, H,CH₂CHCO₂H), 1.43 (s, 3H, CH₃). The regiochemistry of this product is unclear. Yield 17.1% (Ag), 38.6% (Li).

Example 7

By following the procedures set forth above, 2-amido-4-carboxymethyl-4-methyl-5-phenyl-L-pyrrolidine was prepared as shown below:

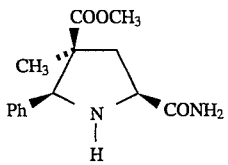

The aldehyde employed in this synthesis was benzaldehyde and the olefin was methyl methacrylate. The support employed in this synthesis was TentaGel RAM resin which, upon treatment with 95% trifluoroacetic acid in methylene chloride, gave the soluble amide derivative. ¹H-nmr data for this compounds is as follows: (DMSO-d₆ 300 MHz) d 7.48–7.20 (m, 5H, ArH), 6.50 (br s, 2H, CONH₂), 5.10 (dd, 1H, CHCONH₂), 4.70 (s 1H,ArCH), 3.65 (s due to glycine), 3.49 (s, 3H, CO₂CH₃), 3.24–3.16 (m, 1H, NH), 2.86 (dd, 1H, CH₂ CHCONH₂), 2.62 (dd, 1H, CH₂CHCONH₂), 1.50 (s, 3H, CH₃). The regiochemistry of this product is unclear. Yield 32.3% (Ag), less than 4.8% (Li)

By following the procedures set forth above, other amino acids can be employed in place of glycine on the solid supports.or peptides of up to about 20 amino acids could be employed merely by substitution of such materials for the glycine/solid support materials described in these examples. Moreover, after completion of the synthesis of the pyrrolidine compound, the amino —NH group of this compound can be acylated using conventional chemistry, including acylation resulting in the incorporation of one or more amino acids thereto.

Likewise, other aldehydes or ketones could be employed in place of the benzaldehyde to provide different substitution at the 5 position of the resulting pyrrolidine compounds.

Alternative Procedure for Pyrrolidine Formation on Resin

TentaGel™ AC pre-loaded with an Fmoc-protected amino acid (0.50 g/loading 0.20–0.26 mmol) was added to a 20% solution of piperidine in dimethylformamide (3 mL) and gently vortexed every 5 minutes for 20 minutes to remove the Fmoc protecting group. The resin was filtered using a fine buchner funnel, washed with dimethylformamide (1×3 mL) and dichloromethane (2×3 mL). The resin was added to a 1.0M solution of aromatic aldehyde in trimethyl orthoformate (4 mL), vortexed gently and left for 4 hours. The resin was again filtered using a fine buchner funnel and washed with dichloromethane (2×3 mL). The resin was then added to a solution of silver(I) nitrate and the appropriate olefin, each at 1.0M. To the solution was added a one molar equivalence of triethylamine and the resulting solution gently vortexed and left for 4–8 hours. The solution turned black after 5–10 minutes with plating of silver upon the walls of the vessel occurring after 2 hours. The resin was filtered using a fine buchner funnel, washed with saturated ammonium chloride (2×3 mL), methanol (2×3 mL) and dichloromethane (2×3 mL). The product was cleaved from the resin by treatment with a 10% solution of trifluoroacetic acid in dichloromethane (2 mL) for 30 minutes. The solution was filtered and evaporated to dryness leaving 19–27 mg of product.

Example 8

By following the procedures set forth above, 4-cyano-5-phenyl-2-pyrrolidinecarboxylic acid was prepared as shown below:

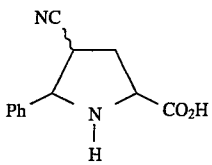

Rotary evaporation afforded 17 mg (71.4%) of a clear colorless oil. Flash chromatography (4" SiO₂, 4:1 petroleum ether/ether) yielded a major product: ¹H NMR (300 MHz, DMSO-d₆) d: 7.70–7.41 (m, 5H, Ph), 5.24 (d, J=7.1 Hz, 1H, H₅), 5.18 (d, J=8.6 Hz, 1H, H₅, a minor epimeric product), 4.73–4.61 (m, 1H, H₂), 4.26–4.18 (m, 1H, H₄), 4.03–2.8 (m, 3H, H₄ (epimer) and H₃).

Example 9

By following the procedures set forth above, 5-phenyl-2, 3,4-pyrrolidinetricarboxylic acid-3,4-dimethyl ester was prepared as shown below:

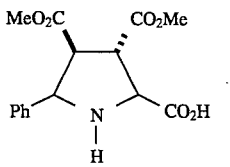

Rotary evaporation afforded 19 mg (61.9%) of a clear colorless oil. Flash chromatography (4" SiO₂, 4:1 petroleum ether/ether) yielded a major product: ¹H NMR (300 MHz, CDCl₃) d: 7.70–7.25 (m, 5H, Ph), 5.16 (d, J=7.4 Hz, 1H, H₅), 4.82 (d, J=7.8 Hz, 1H, H₂), 4.00–3.71 (m, 2H, 1H, H₃ and H₄), 3.69 (s, 3H, 3-CO₂Me), 3.23 (s, 3H, 4-CO₂Me), 2.82 (s, 1H, H ₁).

Example 10

By following the procedures set forth above, 4-methyl-5-phenyl-2,4-pyrrolidinedicarboxylic acid-4-methyl ester was prepared as shown below:

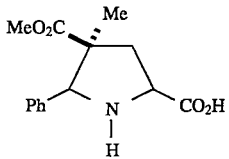

Rotary evaporation afforded 25.5 mg (81.1%) of a clear colorless oil. Flash chromatography (4" SiO₂, 4:1 petroleum ether/ether) yielded a major product: ¹H NMR (300 MHz, DMSO-d₆) d: 7.47–7.20 (m, 5H, Ph), 4.79 (m, 1H, H₂), 4.73 (s, 1H, H₅), 3.49 (s, 3H, CO₂Me), 3.20 (br s, 1H, H₁), 2.86–2.60 (m, 2H, H₃), 1.43 (s, 3H, 4-Me).

By following the procedures set forth above, other amino acids can be employed in place of glycine on the solid supports or peptides of up to about 20 amino acids could be employed merely by substitution of such materials for the glycine/solid support materials described in these examples. Moreover, after completion of the synthesis of the pyrrolidine compound, the amino —NH group of this compound can be acylated using conventional chemistry, including acylation resulting in the incorporation of one or more amino acids thereto.

Likewise, other aldehydes or ketones could be employed in place of the benzaldehyde to provide different substitution at the 5 position of the resulting pyrrolidine compounds.

Mercaptoacyl Pyrrolidine Library Synthesis

TentaGel™ AC resins loaded with Fmoc-protected glycine (0.24 g, 0.0625 mmol)), alanine (0.28 g, 0.0625 mmol), leucine (0.26 g, 0.0625 mmol), and phenylalanine (0.25 g, 0.0625 mmol) resins were pooled and added to a 20 % solution of piperidine in dimethylformamide (3 mL), and gently vortexed every 5 minutes for 20 minutes to remove the Fmoc protecting group. See FIG. 3. The resin was filtered using a fine buchner funnel, washed with dimethylformamide (1-×3 mL) and dichloromethane (2×3 mL). The resin was separated into four equal (by weight) amounts and placed into separate vials.

To each vial of resin was added a 1.0M solution of a separate aromatic aldehyde (benzaldehyde-$^{13}$CHO, 2methoxybenzaldehyde, 2-methylbenzaldehyde, and 2-tert-butyldimethylsilyoxybenazaldehyde) in trimethyl orthoformate. Each solution was vortexed gently and left for 4 hours. The resins were filtered using a fine buchner funnel, added together and vortexed in dichloromethane, refiltered and washed with dichloromethane (2×3 mL). The resin was treated with acetic anhydride (3 mL) and N$^i$Pr$_2$Et (1 mL) for 15 minutes to acylate any unreacted amino acid, then filtered using a fine buchner funnel, vortexed in dichloromethane, refiltered and washed with dichloromethane (2×3 mL). The resin was separated into five equal (by weight) amounts and placed into separate vials.

To each vial of resin was added a 1.0M solution of silver(I) nitrate in acetonitrile followed by the addition of a separate olefin (acrylonitrile, methyl acrylate, tert-butylacrylate, methyl methacrylate, and methyl vinyl ketone) at the concentration of 1.0M. To these solutions was added a one molar equivalence of triethylamine and the resulting solutions were gently vortexed and left for 4–8 hours. The solutions turned black after 5–10 minutes with plating of silver upon the walls of the vessel occurring after 1 hours. The resins were filtered using a fine buchner funnel, mixed together, and washed with saturated ammonium chloride (2×3 mL), methanol (2×3 mL) and dichloromethane (2×3 mL). The resin was separated into three equal (by weight) amounts and placed into separate vials.

To each vial of resin was added a 1.0M solution of triethylamine in tetrahydrofuran for 15 minutes. A one molar equivalence of a separate acetyl-protected mercaptoacyl chloride (2-acetyl mercaptoacetic, 3-acetyl mercaptopropionic, and 2(S)-3-acetyl mercaptoisobutyric) was added dropwise to each vial and the solution vortexed gently for 15 minutes. Each reaction was quenched with the addition of methanol (2 mL). Each resin was filtered using a fine buchner funnel, washed with methanol (2×3 mL) and dichloromethane (2×3 mL). The acylation reaction was repeated to ensure complete coupling. The resins were kept separate and 30 mg of each resin added to a 10% solution of trifluoroacetic acid in dichloromethane (2 mL) for 30 minutes. The solutions were filtered and evaporated to dryness leaving 1–2 mg of each product pool.

To each product was added 200 μA of 1.0M ethylenediamine in methanol under nitrogen. After 20 minutes each pool was transferred to a 1.5 mL eppendorf tube containing 200 μL of 50 mM HEPES pH 8.3 buffer. The reaction vessels were washed with 100μL of methanol and transferred. To each solution was added 2.0M HCl until a pH of 5 was attained, followed by dilution with HEPES buffer to a total volume of 1.00 mL. The ACE inhibitory activity of each pool was immediately determined.

Figure 6:
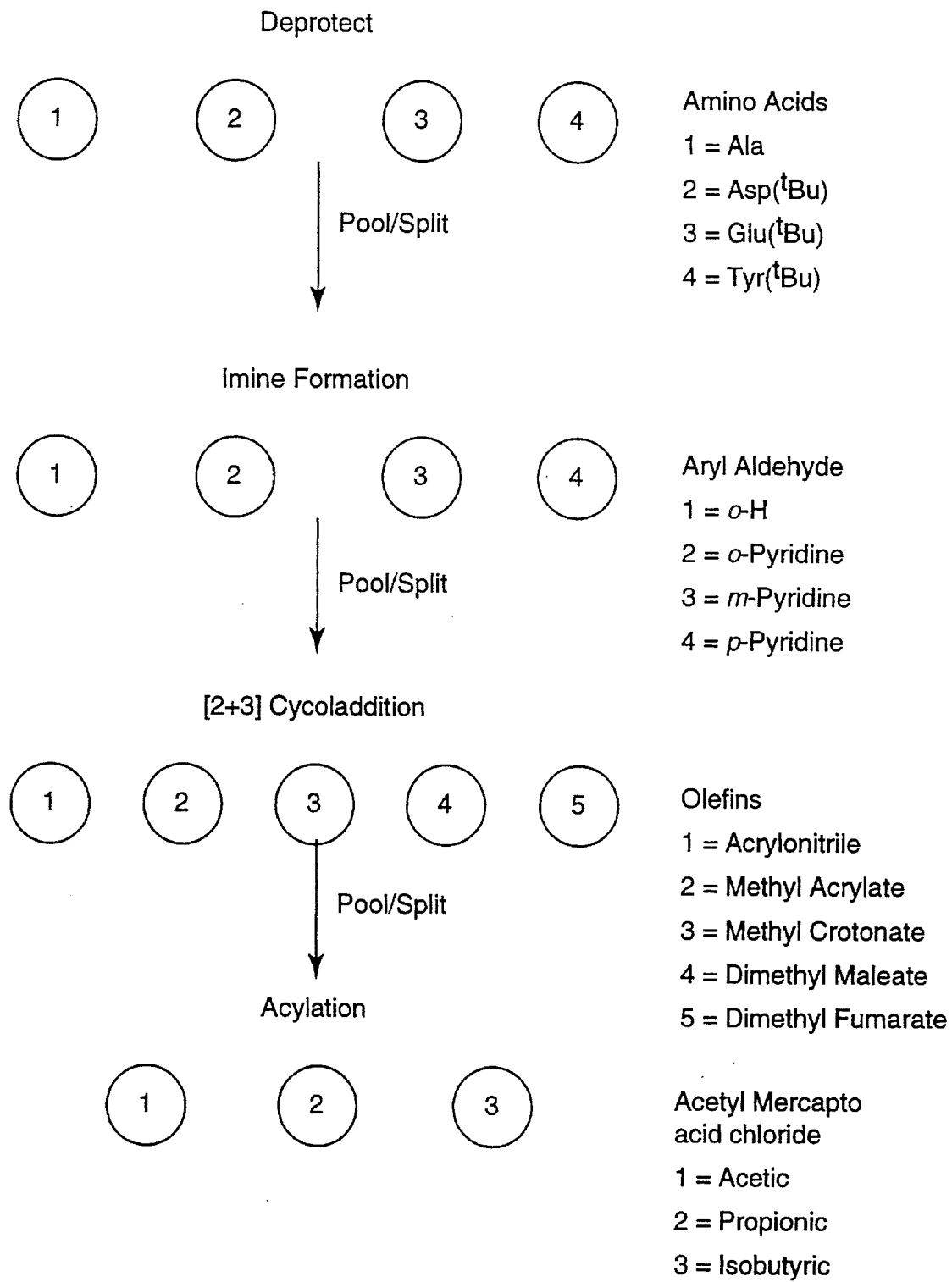
FIG. 6 illustrates a split/pool combinatorial synthesis approach capable of producing a library of mercaptoacyl proline derivatives from amino acid, aldehyde, olefin, and mercapto acid building blocks.

Following the procedures set forth above and substituting the building blocks shown in FIG. 6 for those given above, the corresponding mercaptoacyl proline library was prepared.

Isolation and Characterization of Diastereomeric ACE-Inhibitory Acetylthio-isobutyryl Pyrrolidines (10 and 11) from Solid-Phase Synthesis The mercaptoacyl pyrrolidine synthesis procedure was repeated using glycine, benzaldehyde-$^{13}$CHO, methyl acrylate and 2(S)-3-acetyl mercaptoisobutyryl chloride as the component building blocks as described above. After cleavage from the resin, the crude reaction mixture was analyzed by HPLC and two major product fractions were isolated. These were characterized as diastereomers arising from acylation of a racemic pyrrolidine intermediate (vide infra): 1-(3'-Acetylthio-2'(S)-methyl-1'-oxopropyl)-5(R)-phenyl-2(R),4(R)pyrrolidinedicarboxylic acid-4-methyl ester (10) (Earlier eluting isomer):

$^1$H NMR (300 MHz, CDCl$_3$) d: 7.35–7.25 (m, 5H, Ph), 5.25 (dd, J$_{H-H}$=8.4 Hz, J$_{C-H}$=145.6 Hz, 1H, H$_5$), 4.75 (dd, J=7.5 & 10.9 Hz, 1H, H$_2$), 3.48 (m, 1H, H$_4$), 3.39 (s, 3H, CO$_2$Me), 2.98–2.79 (m, 3H, H$_{3'}$, & H$_{3a}$), 2.72–2.62 (m, 1H, H$_{2'}$), 2.48–2.36 (m, 1H, H$_{3b}$), 1.89 (s, 3H, SAc), 1.27 (d, J=6.9 Hz, 3H, 2'-Me); $^{13}$C NMR (75 MHz, CDCl$_3$) d: 64.068 ($^{13}$C enriched carbon); IR (cm$^{-1}$) 3355.1, 1733.8, 1700.1, 1635.3, 1558.9, 1212.1.

1-(3'-Acetylthio-2'(S)-methyl-1'-oxopropyl)-5(S)-phenyl-2(S),4(S)pyrrolidinedicarboxylic acid-4-methyl ester (11) (Later eluting isomer):

$^1$H NMR (300 MHz, CDCl$_3$) d: 7.40–7.28 (m, 5H, Ph), 5.48 (dd, J$_{H-H}$=8.7 Hz, J$_{C-H}$=146.7 Hz, 1H, H$_5$), 4.61 (dd, J=7.4 & 11.3 Hz, 1H, H$_2$), 3.57 (m, 1H, H$_4$), 3.41 (s, 3H, CO$_2$Me), 3.05 (dd, J=7.6 & 13.6 Hz, 1H, H$_{3'a}$), 2.89 (dd, J=6.7 & 13.6 Hz, 1H, H$_{3'b}$), 2.87–2.60 (m, 2H, H$_{3a}$ & H$_{2'}$), 2.50–2.40 (m, 1H, H$_{3b}$), 2.39 (s, 3H, SAc), 0.81 (d, J=6.7 Hz, 3H, 2'-Me); $^{13}$C NMR (75 MHz, CDCl$_3$) d: 63.904 ($^{13}$C enriched carbon); IR (cm$^{-1}$) 3339.1, 1733.5, 1700.2, 1653.3, 1559.9, 1230.4.

Correlation of Diastereomeric ACE-Inhibitory Acetylthio-isobutyryl Pyrrolidines (10 and 11) with Literature Standards The all-syn relative stereochemistry reported for products (10) and (11) above was established by acylation of racemic syn-5-phenyl-2,4-pyrrolidinedicarboxylic acid-2,4-dimethyl ester, prepared according to literature methods,[32] with 2(S)-3-acetyl mercaptoisobutyryl chloride. To a stirred solution of syn-5-phenyl-2,4-pyrrolidinedicarboxylic acid-2,4-dimethyl ester (0.21 g, 0.80 mmol) in tetrahydrofuran was added triethylamine (0.122 mL, 0.88 mmol). After 15 minutes 2(S)-3-acetyl mercaptoisobutyryl chloride was added dropwise and the reaction mixture stirred for one hour. The reaction was quenched with methanol (2 mL). The addition of 5 mL of diethyl ether was followed by extraction with pH 7 buffer (2×5 mL). The organic layer was dried over anhydrous magnesium sulfate and concentrated by rotary evaporation to afford 0.326 g (98.5%) of a yellow oil. Semi-preparative HPLC afforded two diastereomeric products.

Earlier eluting isomer:

$^1$H NMR (300 MHz, CDCl$_3$) d: 7.64–7.27 (m, 5H, Ph), 5.18 (dd, J$_{H-H}$=8.7 Hz, J$_{C-H}$=145.7 Hz, 1H, H$_5$), 4.42 (dd,

J=6.9 & 11.4 Hz, 1H, $H_2$), 3.87 (s, 3H, 2-$CO_2$Me), 3.60–3.48 (m, 1H, $H_4$), 3.39 (s, 3H, 4-$CO_2$Me), 2.85 (dd, J=5.4 & 13.3 Hz, 1H, $H_{3'a}$), 2.78 (dd, J=8.6 & 13.3 Hz, 1H, $H_{3'b}$), 2.62–2.48 (m, 2H, $H_{2'}$, & $H_{3a}$), 2.43–2.31 (m, 1H, $H_{3b}$), 1.98 (s, 3H, SAc), 1.20 (d, J=6.9 Hz, 3H, 2'-Me); $^{13}$C NMR (75 MHz, $CDCl_3$) d: 63.804 ($^{13}$C enriched carbon); IR (cm$^{-1}$) 1739.3, 1717.3, 1652.7, 1418.9, 1135.4;

Treatment of the mono-ester (10) with ethereal diazomethane in the presence of a trace amount of acetic acid afforded a product with identical spectroscopic parameters and HPLC retention time.

Later eluting isomer:

$^1$H NMR (300 MHz, $CDCl_3$) d: 7.59–7.28 (m, 5H, Ph), 5.43 (dd, $J_{H-H}$=8.7 Hz, $J_{C-H}$=147.1 Hz, 1H, $H_5$), 4.50 (dd, J=6.9 & 11.4 Hz, 1H, $H_2$), 3.84 (s, 3H, 2-$CO_2$Me), 3.68–3.56 (m, 1H, $H_4$), 3.39 (s, 3H, 4-$CO_2$Me), 3.03 (dd, J=7.4 & 13.6 Hz, 1H, $H_{3'a}$), 2.78 (dd, J=7.0 & 13.6 Hz, 1H, $H_{3'b}$), 2.68–2.49 (m, 2H, $H_{2'}$, & $H_{3a}$), 2.46–2.35 (m, 1H, $H_{3b}$), 2.38 (s, 3H, SAc), 0.76 (d, J=6.7 Hz, 3H, 2'-Me); $^{13}$C NMR (75 MHz, $CDCl_3$) d: 63.193 ($^{13}$C enriched carbon); IR (cm$^{-1}$) 1744.2, 1738.4, 1685.4, 1602.7, 1434.8, 1177.1;

Treatment of the mono-ester (11) with ethereal diazomethane in the presence of a trace amount of acetic acid afforded a product with identical spectroscopic parameters and HPLC retention time.

Determination of Enzyme Inhibition for Inhibitor Libraries

Enzyme assays were carried out using a fluorometric assay developed previously.[33] Rabbit kidney ACE (Sigma) (0.01 mL, final concentration 2 nM) in 50 mM HEPES, 0.3M NaCl, pH 8.3 was combined with buffer (0.070 mL), inhibitor library or buffer (0.01 mL), and the substrate solution of Hippuryl-His-Leu, sodium salt (0.01 mL, 10 mM) to give a final substrate concentration of 1 mM. The concentrations of inhibitor libraries were judged on the basis of thiol content as determined using the Ellman assay.[34] Inhibitors were preincubated with the enzyme for 1 hour at room temperature to attain equilibrium prior to the addition of substrate. Reactions were incubated at 37° C. for 4 minutes and quenched by the addition of 0.28N NaOH (1.4 mL). The product, His-Leu, was then derivatized to a fluorophore by the addition of 2% o-phthalaldehyde (0.1 mL) in MeOH, followed by incubation at 25° C. for 8 minutes, addition of 2N HCl (0.2 mL), and then measuring fluorescence after 15 minutes incubation at 25° C.

The fluorescence intensity (arbitrary units) was determined using an SLM Aminco model 8000 spectrofluorometer equipped with a temperature regulated cell using an excitation wavelength at 360 nm and with an emission wavelength at 490 nm. The amount of His-Leu formed with time was determined from standard curves of fluorescence versus concentration of His-Leu (Sigma). The values of inhibitor concentration producing 50% inhibition ($IC_{50}$) were obtained by non-linear least squares regression fits of lines produced by evaluating the % inhibition with varying concentration of inhibitor.

Determination of Inhibition Constants

The kinetics of homogeneous inhibitors and captopril were examined to better define their inhibitory potency. The dissociation constant of the enzyme-inhibitor complex ($K_i$) was determined using the same fluorometric assay and buffer conditions described above, with the exceptions of using 50 pM final enzyme concentration, a 20 minute preincubation time, and assay times of either 10 or 20 minutes. Using these conditions it was found that both 1-(3'-thio-2'(S)-methyl-1'-oxopropyl)-5-phenyl-2,4-pyrrolidinedicarboxylic acid 4-methyl ester (9) and captopril exhibit competitive type inhibition, and that (9) is approximately 3-fold more active than captopril with $K_i$'s of 160 ±50 pM and 475 ±100 pM, respectively. Inhibition constants were determined from double reciprocal plots of rate of product formation versus substrate concentration in the absence and presence of inhibitor.

What is claimed is:

1. A synthetic compound library comprising a plurality of different compounds each compound covalently linked to a solid support wherein each of said compounds comprise at least one pyrrolidinyl group which group is prepared by the method which comprises (a) selecting a solid support comprising at least one compound attached thereto which compound comprises a moiety selected from the group consisting of a complementary group having at least one site of carbon-carbon unsaturation and an azomethine ylide precursor; and (b) converting said moiety to a pyrrolidinyl group.

2. The synthetic compound library according to claim 1 wherein each compound of said plurality of different compounds is covalently linked to the same solid support.

3. The synthetic compound library according to claim 1 wherein each compound of said plurality of different compounds is covalently linked to a different solid support.

4. The synthetic compound library according to claim 1 wherein each compound in said library comprises a peptide compound wherein the pyrrolidinyl group is located at any point in the peptide sequence.

5. The synthetic compound library according to claim 1 wherein each compound in said library comprises a plurality of different pyrrolidinyl compounds.

6. The synthetic compound library according to claim 1, further comprising the step of:

(c) cleaving the compound from the support.

7. The synthetic compound library according to claim 1, further comprising the step of:

(c) treating said pyrrolidinyl group with an acylating reagent.

8. The synthetic compound library according to claim 7, wherein the acylating reagent comprises a compound having the formula:

$HSCH_2CHR^3C(O)X$ wherein $R^3$ is selected from the group consisting of alkyl, alkoxy, carboxyl, carboxyl ester, $R^5$—C(O)— where $R^5$ is alkyl or aryl and X is bromine or chlorine.

9. The synthetic compound library according to claim 8, wherein each compound in said library comprises a different mercaptoacyl proline.

* * * * *